US007244425B2

(12) United States Patent
Liu et al.

(10) Patent No.: US 7,244,425 B2
(45) Date of Patent: Jul. 17, 2007

(54) **ACID- AND BILE SALT-RESISTANT *LACTOBACILLUS* ISOLATES HAVING THE ABILITY TO LOWER AND ASSIMILATE CHOLESTEROL**

(75) Inventors: Yu-Ju Liu, Hsin-Chu (TW); Chin-Chu Yu, Kaohsiung (TW); Ching-Fen Tan, Hsin-Chu (TW); Chii-Cherng Liao, Hsin-Chu (TW)

(73) Assignee: Food Industry Research and Development Institute, Hsin-Chu (TW)

( * ) Notice: Subject to any disclaimer, the term of this patent is extended or adjusted under 35 U.S.C. 154(b) by 0 days.

(21) Appl. No.: 10/684,105

(22) Filed: Oct. 10, 2003

(65) Prior Publication Data
US 2004/0115179 A1 Jun. 17, 2004

(30) Foreign Application Priority Data
Oct. 30, 2002 (TW) ................... 91132189

(51) Int. Cl.
 *A01N 63/00* (2006.01)
 *A01N 65/00* (2006.01)
 *A61K 39/00* (2006.01)
 *A61K 45/00* (2006.01)
 *A61K 38/00* (2006.01)

(52) U.S. Cl. ............... 424/93.45; 424/93.1; 424/184.1; 424/278.1; 530/300; 530/350

(58) Field of Classification Search ............... 530/350, 530/300; 424/184.1, 278.1, 93.1, 93.45
See application file for complete search history.

(56) References Cited

U.S. PATENT DOCUMENTS

| 4,839,281 A | 6/1989 | Gorbach et al. | |
| 5,032,399 A | 7/1991 | Gorbach et al. | |
| 5,516,684 A | 5/1996 | Saito et al. | |
| 5,707,854 A | 1/1998 | Saito et al. | |
| 6,214,336 B1 * | 4/2001 | Bukowska et al. | 424/93.45 |
| 6,399,124 B1 * | 6/2002 | Lesens et al. | 426/61 |
| 2001/0048918 A1 * | 12/2001 | Lievense et al. | 424/93.4 |
| 2003/0147995 A1 * | 8/2003 | Koss et al. | 426/72 |
| 2003/0235559 A1 * | 12/2003 | Sobol et al. | 424/93.4 |

FOREIGN PATENT DOCUMENTS

| EP | 0 792 586 | 4/1999 |
| KR | 2000-0007623 | 2/2000 |

OTHER PUBLICATIONS

A. Sibel Akalin et al. "Influence of Yogurt and Acidophilus Yogurt on Serum Cholesterol Levels in Mice", J. Dairy Sci. 80:2721-2725, 1997.
M. M. Brashears et al. "Influences of pH during growth on removal of cholestoral from MRS broth by *Lactobacillus casei* and *Lactobacillus acidophillus*". OSU Research Report 5:1-5, 1997.
A. D. Danielson et al. "Anticholesteremic Property of *Lastobacillus acidophilus* Yogurt Fed to Mature Boars". J. Amin. Sci. 67:966-974, 1989.
J. Denter et al. "Formation of B-vitamins by bacteria during the soaking process of soybeans for tempe fermentation". International Journal of Food Microbiology 22:23-31, 1994.
G. H. Fleet et al. "Evolution of Yeasts and Lactic Acid Bacteria During Fermentation and Storage of Bordeaux Wines". Applied and Environmental Microbiology 48:1034-1038, Nov. 1984.
S. E. Gilliland et al. "Assimilation of Cholesterol by *Lastobacillus acidophilus* ". Applied and Environmental Microbiology 49(2):377-381, Feb. 1985.
S. W. Gilliland et al. "Factors to Consider When Selecting a Culture of *Lactobacillus acidophilus* as a Dietary Adjunct to Produce a Hypocholesterolemic Effect in Humans". Journal Series of the Oklahoma Agriculture Experiment Station, Stillwater, OK, Paper No. 5596, Sep. 25, 1989.
K. K. Grunewald. "Serum Cholesterol Levels in Rats Fed Skim Milk Fermented by *Lactobacillus Acidophilus* ". Journal of Food Science 47:2078-2079, 1982.
L. L. Rudel et al. "Determination of cholesterol using o-phthalaldehyde". Journal of Lipid Research 14:364-366, 1973.
M. G. O'Sullivan et al. "Probiotic bacteria: myth or reality?" Trends in Food Science & Technology 3:309-314, Dec. 1992.
F. A. M. Klaver et al. "The Assumed Assimilation of Cholesterol by *Lactobacillus* and *Bifidobacterium bifidum* Is Due to Their Bile Salt-Deconjugating Activity". Applied and Environmental Microbiology 59(4): 1120-1124, Apr. 1993.
S. Razin et al. "Phospholipid and Cholesterol Uptake by Mycoplasma Cells and Membranes", Biochimica et Biophysica Acta 598:628-640, 1980.
I. De Smet et al. "Cholesterol lowering in pigs through enhanced bacterial bile salt hydrolase activity". Journal of Nutrition 79:185-194, 1998.
Usman et al. "Bile Tolerance, Taurocholate Deconjugation, and Binding of Cholesterol by *Lactobacillus gasseri* Strains". J. Dairy Sci. 82:243-248, 1999.
Usman et al. "Viability of *Lactobacillus gasseri* and Its Cholesterol-Binding and Antimutagenic Activities During Subsequent Refrigerated Storage in Nonfermented Milk". J. Dairy Sci. 82:2536-2542, 1999.
D. K. Walker et al. "Relationships Among Bile Tolerance, Bile Salt Deconjugation, and Assimilation of Cholesterol by *Lactobacillus acidophilus* ". J. Dairy Sci. 76:956-961, 1993.
D. G. Noh et al. "Incorporation of Cholesterol into the Cellular Membrane of *Lactobacillus acidophilus* ATCC 43121".
J. C. Zhang et al. "Cholesterol Removal From Foods Using Lactic Acid Bacteria". Food Science (China) 19(3):20-22, 1998. (English Abstract with Chinese article.).
Usman et al. "Viability of *Lactobacillus gasseri* and its cholesterol-binding and antimutagenic activities during subsequent refrigerated storage in nonfermented milk", J. Dairy Sci. 82:2536-2542, 1999.
Plockova et al. "The pH tolerance, bile resistance and production of antimicrobial compounds by Lactobacilli*". Potravinarske Vedy 14(3):165-174, 1996.
Luchansky et al. "Molecular cloning and deoxyribonucleic acid polymorphisms in *Lactobacillus acidophilus* and *Lactobacillus gasseri* ". Journal of Dairy Science 74(10):3293-3302, Oct. 1, 1991.

* cited by examiner

*Primary Examiner*—Robert A. Zeman
*Assistant Examiner*—Lakia J. Tongue
(74) *Attorney, Agent, or Firm*—Occhiuti, Rohlicek & Tsao LLP

(57) ABSTRACT

Disclosed are acid- and bile salt-resistant *Lactobacillus* isolates having the ability to lower cholesterol. The present *Lactobacillus* isolates or their sub-cultured offspring or mutants derived therefrom can be used in the preparation of various food products, and in the manufacture of medicaments for use in the treatment or prevention of gastrointestinal diseases and for use in lowering serum cholesterol.

9 Claims, 5 Drawing Sheets

```
CAGGACGAAC GCTGGCGGCG TGCCTAATAC ATGCAAGTCG AGCGAGCTTG
CCTAGATGAA TTTGGTGCTT GCACCAAATG AAACTAGATA CAAGCGAGCG
GCGGACGGGT GAGTAACACG TGGGTAACCT GCCCAAGAGA CTGGGATAAC
ACCTGGAAAC AGATGCTAAT ACCGGATAAC AACACTAGAC GCATGTCTAG
AGTTTAAAAG ATGGTTCTGC TATCACTCTT GGATGGACCT GCGGTGCATT
AGCTAGTTGG TAAGGTAACG GCTTACCAAG GCAATGATGC ATAGCCGAGT
TGAGAGACTG ATCGGCCACA TTGGGACTGA GACACGGCCC AAACTCCTAC
GGGAGGCAGC AGTAGGGAAT CTTCCACAAT GGACGCAAGT CTGATGGAGC
AACGCCGCGT GAGTGAAGAA GGGTTTCGGC TCGTAAAGCT CTGTTGGTAG
TGAAGAAAGA TAGAGGTAGT AACTGGCCTT TATTTGACGG TAATTACTTA
```

FIG. 5

```
CAGGACGAAC GCTGGCGGCG TGCCTAATAC ATGCAAGTCG AGCGAGCTTG
CCTAGATGAA TTTGGTGCTT GCACCAAATG AAACTAGATA CAAGCGAGCG
GCGGACGGGT GAGTAACACG TGGGTAACCT GCCCAAGAGA CTGGGATAAC
ACCTGGAAAC AGATGCTAAT ACCGGATAAC AACACTAGAC GCATGTCTAG
AGTTTAAAAG ATGGTTCTGC TATCACTCTT GGATGGACCT GCGGTGCATT
AGCTAGTTGG TAAGGTAACG GCTTACCAAG GCAATGATGC ATAGCCGAGT
TGAGAGACTG ATCGGCCACA TTGGGACTGA GACACGGCCC AAACTCCTAC
GGGAGGCAGC AGTAGGGAAT CTTCCACAAT GGACGCAAGT CTGATGGAGC
AACGCCGCGT GAGTGAAGAA GGGTTTCGGC TCGTAAAGCT CTGTTGGTAG
TGAAGAAAGA TAGAGGTAGT AACTGGCCTT TATTTGACGG TAATTACTTA
```

FIG. 6

```
CAGGACGAAC GCTGGCGGCG TGCCTAATAC ATGCAAGTCG AGCGAGCTTG
CCTAGATGAA TTTGGTGCTT GCACCAAATG AAACTAGATA CAAGCGAGCG
GCGGACGGGT GAGTAACACG TGGGTAACCT GCCCAAGAGA CTGGGATAAC
ACCTGGAAAC AGATGCTAAT ACCGGATAAC AACACTAGAC GCATGTCTAG
AGTTTAAAAG ATGGTTCTGC TATCACTCTT GGATGGACCT GCGGTGCATT
AGCTAGTTGG TAAGGTAACG GCTTACCAAG GCAATGATGC ATAGCCGAGT
TGAGAGACTG ATCGGCCACA TTGGGACTGA GACACGGCCC AAACTCCTAC
GGGAGGCAGC AGTAGGGAAT CTTCCACAAT GGACGCAAGT CTGATGGAGC
AACGCCGCGT GAGTGAAGAA GGGTTTCGGC TCGTAAAGCT CTGTTGGTAG
TGAAGAAAGA TAGAGGTAGT AACTGGCCTT TATTTGACGG TAATTACTTA
```

FIG. 7

```
CAGGACGAAC GCTGGCGGCG TGCCTAATAC ATGCAAGTCG AGCGAGCTTG
CCTAGATGAT TTTGGTGCTT GCACTAAATG AAACTAGATA CAAGCGAGCG
GCGGACGGGT GAGTAACACG TGGGTAACCT GCCCAAGAGA CTGGGATAAC
ACCTGGAAAC AGATGCTAAT ACCGGATAAC AACACTAGAC GCATGTCTAG
AGTTTGAAAG ATGGTTCTGC TATCACTCTT GGATGGACCT GCGGTGCATT
AGCTAGTTGG TAAGGTAACG GCTTACCAAG GCAATGATGC ATAGCCGAGT
TGAGAGACTG ATCGGCCACA TTGGGACTGA GACACGGCCC AAACTCCTAC
GGGAGGCAGC AGTAGGGAAT CTTCCACAAT GGACGAAAGT CTGATGGAGC
AACGCCGCGT GAGTGAAGAA GGGTTTCGGC TCGTAAAGCT CTGTTGGTAG
TGAAGAAAGA TAGAGGTAGT AACTGGCCTT TATTTGACGG TAATTACTTA
```

FIG. 8

```
CAGGACGAAC GCTGGCGGCG TGCCTAATAC ATGCAAGTCG AGCGAGCTTG
CCTAGATGAA TTTGGTGCTT GCACCAAATG AAACTAGATA CAAGCGAGCG
GCGGACGGGT GAGTAACACG TGGGTAACCT GCCCAAGAGA CTGGGATAAC
ACCTGGAAAC AGATGCTAAT ACCGGATAAC AACACTAGAC GCATGTCTAG
AGTTTAAAAG ATGGTTCTGC TATCACTCTT GGATGGACCT GCGGTGCATT
AGCTAGTTGG TAAGGTAACG GCTTACCAAG GCAATGATGC ATAGCCGAGT
TGAGAGACTG ATCGGCCACA TTGGGACTGA GACACGGCCC AAACTCCTAC
GGGAGGCAGC AGTAGGGAAT CTTCCACAAT GGACGCAAGT CTGATGGAGC
AACGCCGCGT GAGTGAAGAA GGGTTTCGGC TCGTAAAGCT CTGTTGGTAG
TGAAGAAAGA TAGAGGTAGT AACTGGCCTT TATTTGACGG TAATTACTTA
```

FIG. 9

```
B6T7  CA - GACGAAC  GCTGGCGGCG  TGCCTAATAC  ATGCAAGTCG  AGCG - AC - CT
La    CAGGACGAAC   GCTGGCGGCG  TGCCTAATAC  ATGCAAGTCG  AGCG - AG - CT
Lp    CAGGACGAAC   GCTGGCGGCG  TGCCTAATAC  ATGCAAGTCG  AACGAACTCT
      . . * . . . . . . . . . . . . . . . . . . . . . . . . . . . . . . . . * . . * . * * . .

B6T7  - GAACCAACA  GAT - - TCACT  TCGGTGA - TG  ACGTTGGGAA  CGCGAGCGGC
La    - GAACCAACA  GAT - - TCACT  TCGGTGA - TG  ACGTTGGGAA  CGCGAGCGGC
Lp    GGTATTGATT   GGTGCTTGCA  TC - ATGATTT  ACATT - TG - A - GTGAGTGGC
      * . * . * * * . * * . * . * * . * * . . . * . . . . * . . . * . . . * * . * . * . * . . . . * . . .

B6T7  GGATGGGTGA   GTAACACGTG  GGGAACCTGC  CCCAT - AGTC  TGGGATACCA
La    GGATGGGTGA   GTAACACGTG  GGGAACCTGC  CCCAT - AGTC  TGGGATACCA
Lp    GAACTGGTGA   GTAACACGTG  GGAAACCTG - CCCAGAAGCG  GGGGATAACA
      . * . * * . . . . . . . . . . . . . . . . . * . . . . . . * . . . . * * . . * * . . . . . . . . . * . .

B6T7  CTTGGAAACA   GGTGCAATA   CCGGATAAGA  AAGCAGATGC  CATGATCAGC
La    CTTGGAAACA   GGTGCAATA   CCGGATAAGA  AAGCAGATGC  CATGATCAGC
Lp    CCTGGAAACA   GATGCTAATA  CCGCATAACA  ACTTGGACCG  CATGGTCCGA
      . * . . . . . . . . . . * . . . . . . . . . . . * . . . . * . . * * * * . . . * . . . . . . . . * . . . * . *

B6T7  TTATAAAAGG   CGGCGTAAGC  TGTCGCTATG  GGATGGCCCC  GCGGTGCATT
La    TTATAAAAGG   CGGCGTAAGC  TGTCGCTATG  GGATGGCCCC  GCGGTGCATT
Lp    G - TTGAAAGA  TGGCTTCGGC  TATCACTTTT  GGATGGTCCC  GCGGCGTATT
      * * * . * . . . . * . * . . . . . . . . . . . * . . . . . . . . . . . . . * . . . . . * * * * . . * . .

B6T7  AGCTAGTTGG   TAGGGTAACG  GCCTACCAAG  GCAATGATGC  ATAGCCGAGT
La    AGCTAGTTGG   TAGGGTAACG  GCCTACCAAG  GCAATGATGC  ATAGCCGAG -
Lp    AGCTAGATGC   TGGGGTAACG  GCTCACCATG  GCAATGATAC  GTAGCCGA - C
      . . . . * . . * . . * . * * * * . * . . . . * . . * . * * . . . * . . * . . * . . . . . . . . * . . .

B6T7  TTGAGAGACT   GATCCGGCCA  CATTGGGACT  GAGACACGGC  CCAAACTCCT
La    TTGAGAGACT   GAT - CGGCCA  CATTGGGACT  GAGACACGGC  CCAAACTCCT
Lp    CTGAGAGGGT   AAT - CGGCCA  CATTGGGACT  GAGACACGGC  CCAAACTCCT
      * . . . . . . * * . . * . . . * . . . . . . . . . . . . . . . . . . . . . . . . . . . . . . . . . . . . .

B6T7  ACGGGAGGGC   AAGCAGTAGG  GAATCCTCCA  CAATGGACCA  AAGTCCTGAT
La    ACGGGA - GGC  - AGCAGTAGG  GAATCTTCCA  CAATGGACGA  AAGT - CTGAT
Lp    ACGGGA - GGC  - AGCAGTAGG  GAATCTTCCA  CAATGGACGA  AAGT - CTGAT
      . . . . . . * . . . * . . . . . . . . . . . . . . . * . . . . . . . . . . . . . . * . . . . . . * . . . . .

B6T7  GGAGCAACGC   CCCGTGAGTT  GAAGAA - GTT  TTCGGATCGT  AAAGCCCTGT
La    GGAGCAACGC   CGCGTGAG - T  GAAGAAGGTT  TTCGGATCGT  AAAGCTCTGT
Lp    GGAGCAACGC   CGCGTGAG - T  GAAGAAGGGT  TTCGGCTCGT  AAAACTCTGT
      . . . . . . . . . . . * . . . . . . . * . . . . . . * . * . . . . . . . * . . . . . . . . . . * . . * . . . .

B6T7  TGTTGGTGAA   GAAGGATA - G  AGGTAAGAAC  TG - GCCTTTA  TTTGACCGTA
La    TGTTGGTGAA   GAAGGATA - G  AGGTAGTAAC  TG - GCCTTTA  TTTGACGGTA
Lp    TGTTAAAGAA   GAA - CATATC  TGAGAGTAAC  TGTTCAGGTA - TTGACGGTA
      . . . . * * . . . . * * . . . * * * . . . * * . . * * . . * * . . . . * . . . * * . * * * . . . * . . . * . . .
```

FIG. 10

ACID- AND BILE SALT-RESISTANT *LACTOBACILLUS* ISOLATES HAVING THE ABILITY TO LOWER AND ASSIMILATE CHOLESTEROL

BACKGROUND OF THE INVENTION

1) Field of the Invention

The present invention relates to novel gastric acid- and bile salt-resistant *Lactobacillus* isolates having the ability to lower and assimilate serum cholesterol and the to use thereof.

2) Description of the Related Art

"Lactic acid bacteria" are a group of bacteria that can ferment saccharides and that produce lactic acid as a major product. The generally accepted morphological and physiological characteristics of lactic acid bacteria reside in that they are: (1) Gram positive; (2) rod-shaped or disk-shaped; (3) catalase-negative; (4) capable of converting metabolized glucose into more than 50% of lactic acid; (5) nonspore-forming; (6) nonmotile; and (7) microaerobic.

Up to 1980, lactic acid bacteria were known to include, in general, four genera, namely, *Lactobacillus, Streptococcus, Leuconostoc* and *Pediococcus* (W. C. Frazier and D. C. Westhoff, 1978, Food Microbiology, 3rd ed. McGraw-Hill, Inc., New York, USA). In a broader sense, lactic acid bacteria further comprise two genera of *Bifidobacterium* and *Sporolactobacillus*. In recent years, microorganisms have been explicitly classified as a taxonomic group according to DNA homology and rDNA sequence comparison and analysis in the classification system, and have been given a position in taxonomy. To Applicants' knowledge, the family of lactic acid bacteria has expanded to include 16 genera and 223 species by December 1999.

The so-called "probiotics" are live bacteria of a single type or a mixture of bacteria of different types which, after being ingested by the human or animal host, can improve gastrointestinal microbial balance in the human or animal intestinal tract (O'sullivan et al. (1992), *Trends in Food Sci. Technol.*, 3:309-314; Fuller, R., P. J. Heidt, V. Rush and D. van der Waaij. (eds.) (1995), *Probiotics: prospects of use in opportunistic infections. Old Herborn University Seminar Monograph No. 8*, pp. 1). *Lactobacillus* and *Bifidobacterium* are the most widely known and used probiotics.

In 1908, Dr. Eli Metchnikoff proposed the theory that the consumption of large amounts of yogurt containing strains of *Lactobacillus* sp. would result in the replacement of toxic-producing bacteria normally present in the intestine, and would thus result in longevity-without-aging (Eli Metchnikoff, 1908, *The Prolongation Of Life*, Ed. P. Chalmers Mitchell, G. P. Putnam's Sons, *The Knickerbocker Press*, New York & London). Recent studies and clinical tests have also shown that *Lactobacillus* is critically related to health. Therefore, *Lactobacillus* has received wide attention in recent years.

Lactic acid bacteria not only play an important role in the complex biosystem of the intestines, they also have probiotic effects on the host. The recognized effects of lactic acid bacteria include: improving nutritional value of host feed; promoting the synthesis of vitamins and the production of enzymes (J. Denter and B. Bisping, 1994, *Int. J. Food Microbiol.*, 22:23-31), inhibiting the growth of intestinal pathogenic bacteria and maintaining the balance of normal intestinal microflora (Hose, H. and Sozzi, T. (1991), *J. Chem. Technol. And Biotech.* 51:540-544), producing antibodies to enhance immunity of the host (H. Majamaa et al. (1995), *Journal of Pediatric Gastro-enterology and Nutrition*, 20:333-338), reducing the risk of colon cancer, and suppressing tumor formation (E. J. Schiffrin et al., 1997, *Am. J. Clin. Nutr.*, 66:515S-520S). Researches also show that consumption of milk fermented with *Lactobacillus* can lower serum cholesterol levels.

Cardiovascular disease has been indicated as a major leading cause of death in industrial countries. In the United States, more people died of coronary heart disease than those of cancer and other diseases, and about three-quarters of the deaths are caused by atherosclerosis and complications thereof. High serum cholesterol level is one of the causes of cardiovascular diseases and atherosclerosis (Kannel et al. (1979), *Ann. Intern. Med.*, 90:85-91; Pekkanen et al. (1990), *New England J. Med.*, 322: 1700-1707). In Taiwan, cerebrovascular and cardiovascular diseases are on the list of top ten leading causes of death, and are the major causes of illness and death in old people. Therefore, hypercholesterolemia is a cause of illness that should not be ignored.

In 1974, Mann and Spoerry found that serum cholesterol levels in men decreased after consumption of yogurt fermented with a *Lactobacillus* strain, whereas no significant change was observed in those that consumed fresh milk (*Am. J. Clin. Nutr.*, 27:464-469, 1974), which spurred extensive researches on the application of lactic acid bacteria and their effects in lowering cholesterol.

K. K. Grunewald reported in *J. of Food Science*:47:2078-2079 (1982) that the serum cholesterol level in rats could be significantly decreased when the rats were given feeds containing 10% milk fermented by *Lactobacillus acidophilus* for four weeks. It was also reported by Danielson et al. in *J. Anim. Sci.*: 67:966-974 (1989) that *acidophilus* yogurt reduced serum cholesterol and low density lipoproteins (LDLs) in boars fed with a high-cholesterol diet in combination with yogurt fermented with *Lactobacillus acidophilus* LA16 isolates for a period of 56 days, but had no effect on serum triglycerides and high density lipoproteins (HDLs).

The aforesaid report, which is related to an isolate strain of *Lactobacillus acidophilus*, LA16, is one of the many works by the research group headed by Dr. Khem M. Shahani on the characteristics and bioactivities of *Lactobacillus acidophilus*. Specifically, Dr. Shahani's group had conducted fairly extensive researches on the characteristics and bioactivities of a specially isolated and cultured strain of *Lactobacillus acidophilus* DDS-1 of human origin, including studies on its effect in reducing serum cholesterol level. The DDS-1 isolated strain was later patented (information regarding DDS-1™ is available on the website of Nebraska Cultures, Inc.

In 1997, Akalin et al. compared the effects of ordinary yogurt (fermented by *Streptococcus thermophilus* and *Lactobacillus delbrueckii* ssp. *bulgaticus*) and *acidophilus* yogurt (fermented by *Streptococcus thermophilus* and *Lactobacillus acidophilus*) on serum cholesterol levels in mice, and found that the ability of *acidophilus* yogurt to reduce serum cholesterol concentrations was significantly higher than that of the ordinary yogurt (A. S. Akalin et. al. (1997), *J. Dairy Sci.*, 80:2721-2725).

De Smet et al. reported in *British J. of Nutrition*, 79:185-194 (1998), that the fecal output of bile salts in pigs fed with *Lactobacillus acidophilus* for four weeks (from week 3 to week 7) increased significantly, and the total serum cholesterol concentrations in the pigs also decreased significantly. It was therefore concluded that the enzymatic activity of bile salt hydrase (BSH, E.C.3.5.1.24) within *Lactobacillus* might be the mechanism responsible for lowering serum cholesterol in the treated pigs.

Cholesterol in humans can be synthesized by the liver, and can also be ingested from meat. There are two pathways for the excretion of cholesterol: (1) forming cholic acid as a result of liver metabolism, which is then conjugated with glycine or taurine to become water-soluble and to subsequently form bile salts such as glycocholates or taurocholates, with potassium or sodium ions for excretion in feces; and (2) forming steroid hormones that are excreted in urine as a result of hormone metabolism; however, only a small portion of the cholesterol is excreted in this manner.

Bile salts are water-soluble final products in cholesterol metabolism. These salts may enter the enterohepatic circulation and, because of the enzymatic activity of bile salt hydrase (BSH) of enteric bacteria, including *Lactobacillus, Enterococcus, Peptostreptococcus, Bifidobacterium, Clostridium* and *Bacteroid*, etc., cholic acids can be separated from glycine or taurine to yield deconjugated bile salts. The deconjugated bile salts do not dissolve in water, and are likely to co-precipitate with serum cholesterol for excretion out of the body.

In addition to the aforesaid, it is reported that the metabolism mechanism of cholesterol includes both assimilation and co-precipitation.

In 1985, it was pointed out that *Lactobacillus acidophilus* could adhere to and assimilate cholesterol, and that, in a medium containing 0.3% oxgall, *Lactobacillus acidophilus* could achieve a higher cholesterol reduction (S. E. Gilliland et al. (1985), Appl. Environ. Microbiol, 49: 377-381). Likewise, it was reported by Noh et al. in *J. Dairy Sci.* (1997), 82: 3107-3113 that *Lactobacillus acidophilus* was able to incorporate cholesterol into cellular membranes, and the incorporated cholesterol could be further assimilated and metabolized to form substances required by the cells.

On the other hand, it was reported by F. A. M. Kalver and R. van der Meer in *Appl. Environ. Microbiol.* (1993), 59: 1120-1124 that *Lactobacillus* and *Bifidobacterium* could not assimilate cholesterol, but were able to reduce cholesterol contents in a medium by increasing the conjugating activity of bacterial bile salts when the pH value was below 6.0 to result in co-precipitation of cholesterol with bile salts (this phenomenon may be related to the BSH activity of the bacteria).

In 1997, M. M. Brashears and S. E. Gililland indicated that *Lactobacillus* exhibited good cholesterol co-precipitation during growth without pH control (i.e., at a normal pH of 4.5 to 5.5). However, if the pH value was maintained at about 6.0, the ability of said bacteria to remove cholesterol is significantly decreased (M. M. Brashears and S. E. Gililland (1997), Influences of pH during growth on removal of cholesterol from MRS broth by *Lactobacillus casei* and *Lactobacillus acidophilus*, Animal Science Research Report, pp. 32-37).

In 1998, Zhang Jia-cheng et al. tried to prove that "assimilation" is the major mechanism in the reduction of cholesterol by lactic acid bacteria by experimenting with high lipid milk and edible oil (Zhang Jia-cheng et al. (1998), "The research of cholesterol elimination in food by lactic acid bacteria—the screening of lactic acid bacteria species (strains)," Food Science (P.R.O.C), 19:20-22).

In 1999, Usman and Hosono indicated in *J. Dairy Sci.*, 82: 243-248 that a newly found *Lactobacillus* species, *Lactobacillus gasseri*, can take up cholesterol under culture conditions without bile salts.

Using a biological method to reduce serum cholesterol levels in humans will be more economical and effective. It is apparent from the aforesaid references that lactic acid bacteria may exhibit the effect of reducing cholesterol both in vivo and in vitro, and the possible mechanisms include deconjugation by bile salt hydrase (BSH), co-precipitation of cholesterol with deconjugated bile salts under acidic conditions, and assimilation of cholesterol by lactic acid bacterial cells.

However, after being ingested into the human body, lactic acid bacteria encounter pressure from the gastrointestinal environment and specificity of intestinal absorption. Therefore, lactic acid bacteria have to first overcome the unfavorable environment of the digestive system and colonize the intestinal tract in order to grow and exert their reaction(s) in the intestinal tract. Further, *Lactobacillus acidophilus* strains are a group of bacteria having complex nutritional requirements. The bacteria are relatively stable in fermented milk. However, the bacteria in commercially available products (in forms of dry powder, grains, tablets) can hardly remain viable after long-term storage at room or refrigerated temperature so that the level of the bacteria cannot be easily maintained at an initial storage level. Accordingly, the actual number of bacteria in a non-fermented milk product is often less than that indicated on the product label. Hence, how to maintain the level of lactic acid bacteria in lactic acid bacteria products during marketing and storage is of utmost importance to manufacturers. Furthermore, screening bacteria to obtain bacterial strains having good resistance to acids and bile salts and capable of lowering serum cholesterol is an important subject in the development of excellent *Lactobacillus* products.

As mentioned above, if resistance to acids and bile salts and storage stability are taken into account when screening bacteria, cost savings can be achieved in the subsequent manufacturing process, and the screened bacterial strains can have a wider range of applications. In addition, the screening for effective bacterial strains is also related to origin and locality. Therefore, in recent years, investigators' efforts have focused on the screening of bacterial strains of human origin.

In Japan, in a total of 171 FOSHU (Foods for Specified Health Use)-approved products, 36 contain probiotic bacteria. They make up about 21% of the total number of products, but have a production value of up to 82%. In Europe, the production value of probiotic bacteria in the food market amounts to 1 billion US dollars. In the United States, yogurt sales in 2000 were up to 1.86 billion US dollars. In Taiwan, the probiotic bacteria market grew to NT$ 4.2 billion dollars in 2000. The applications of probiotic bacteria have increased every year and are no longer restricted to fermented milk, milk, ice cream, candies, and dietary supplements. The products are consumed by adults, infants, poultry, and livestock. It is anticipated that there is huge room for growth of the probiotic market.

There are a number of studies on lactic acid bacteria worldwide. Many of the patents and publications on the acid tolerance and cholesterol lowering ability of *Lactobacillus* sp. are directed to *Lactobacillus acidophilus*, and are largely concerned with bile- and acid-resistant bacterial strains, or are mainly focused on their ability to reduce cholesterol and bile tolerance. At present, studies carried out on the bile tolerance of *Lactobacillus* sp. emphasize that the bacterial strains can grow in an environment containing 0.3% glycocholate, and acid tolerance is tested using media at pH 2, the acidic condition occurring in the gastrointestinal tract at the initial stage of gastric juice secretion.

The ability of *Lactobacillus* sp. to reduce serum cholesterol is about 20% according to published patents, and is in the range from about 10% to about 80%, depending on the methods used, according to publications.

U.S. Pat. Nos. 4,839,281 and 5,032,399 disclose a strain, *L. acidophilus* GG (ATCC 53103), which was isolated from human feces. This strain can grow in an environment containing 0.15% bile salts, and the amount of residual bacteria after being cultured for 2 hours at pH 1-2 is $10^3$ CFU.

It was reported by S. E. Gilliland and D. K. Walker in *J. Dairy Sci.*: 73:905-911 (1990) that *L. acidophilus* ATCC 43121 (corresponding to CCRC 17064) of pig origin and *L. acidophilus* ATCC 4356 (corresponding to CCRC 10695) of human origin can both grow in MRS broth supplemented with 0.3% bile salts and have the ability to reduce serum cholesterol.

Further, *L. acidophilus* LA16, the strain isolated from pigs as reported by Danielson et al. in *J. Anim. Sci.* (1989), 67:966-974, and *Lactobacillus acidophilus* DDS-1, an isolated strain of human origin (an endogenous human strain), which was developed by scientists headed by Dr. Khem M. Shahani and which is now a patented product of Nebraska Cultures, Inc., have demonstrated the ability to reduce serum cholesterol.

Usman and Hosono reported in *J. Dairy Sci.*, 82: 243-248 (1999) that an isolated *Lactobacillus* strain *Lactobacillus gasseri* exhibited resistance to acids and bile salts and the ability to reduce cholesterol.

In U.S. Pat. Nos. 5,516,684 and 5,707,854, Yoshio Saito and Jun Mizutani disclose two strains of *L. acidophilus*, namely, *L. acidophilus* FERM-P-14204 and *L. acidophilus* FERM-P-14205. These strains do not exhibit deconjugation of bile acids and do not inhibit nutrient absorption, but they demonstrate the lowering of cholesterol in blood and liver.

However, the aforesaid *Lactobacillus* strains are of foreign origin. It would be desirable to obtain *Lactobacillus* isolates which are acid- and bile-resistant and which are capable of lowering serum cholesterol by screening bacteria strains in Taiwan so that the isolates thus obtained can adapt to the gastrointestinal environment of the people of Taiwan and, when used as starters or when added to processed products, can reach the intestine and colonize the intestine after ingestion to thereby enhance the functionality of the products.

SUMMARY OF THE INVENTION

Accordingly, in the first aspect, the present invention provides *Lactobacillus* isolates having characteristics that include acid and bile tolerance, and good ability to reduce serum cholesterol by screening samples from human subjects in Taiwan.

In the present invention, feces specimens from healthy infants were used as origins of the bacterial strains. The specimens were screened to isolate bacterial strains capable of resisting acids and bile salts in the gastrointestinal environment and lowering cholesterol. As a result, 6 novel *Lactobacillus* isolates having the aforementioned characteristics were obtained, namely, *Lactobacillus gassrei* B21T1, B21T6, C21T1, X21B7 and B38T38, and *L. acidophilus* B6T7. These isolates were deposited in the Food Industry Research and Development Institute (FIRDI, 331 Shih-Pin Road, Hsinchu City 300, Taiwan, R.O.C.) on Jun. 18, 2002, under Accession Nos. CCRC 910195, CCRC 910196, CCRC 910198, CCRC 910199, CCRC 910197 and CCRC 910194, respectively. These isolates were also deposited in the American Type Culture Collection (ATCC, P.O. Box 1549, Manassas, Va. 20108, USA) under the Budapest Treaty on Jun. 21, 2002, and were given ATCC Accession Nos. PTA-4483, PTA-4484, PTA-4479, PTA-4480, PTA-4481 and PTA-4482, respectively.

The novel *Lactobacillus* isolates according to the present invention exhibited a higher cholesterol-lowering ability, as compared to previously known *L. acidophilus* ATCC 43121, ATCC 4356 and DDS-1.

In the second aspect, the present invention provides a composition comprising at least one of the novel *Lactobacillus* isolates according to the present invention or its sub-cultured offspring or a mutant derived therefrom, and an excipient suitable for the manufacture of foodstuffs, such as beverages, cakes, infant foods, fermented milk, dietary supplements, and animal feed.

According to the third aspect, the present invention provides a pharmaceutical composition comprising at least one probiotically effective amount of one of the novel *Lactobacillus* isolates according to the present invention or its subcultured offspring or a mutant derived therefrom for treating and preventing gastrointestinal diseases as well as lowering serum cholesterol.

BRIEF DESCRIPTION OF THE DRAWINGS

The above and other objects and features of the present invention will become apparent with reference to the following description of the preferred embodiments taken in conjunction with the accompanying drawings, in which:

FIG. 5 shows the nucleotide sequence of the 16S rDNA of a bacterial isolate according to the present invention, *Lactobacillus gasseri* B21T1 (SEQ ID NO:1);

FIG. 6 shows the nucleotide sequence of the 16S rDNA of a bacterial isolate according to the present invention, *Lactobacillus gasseri* B21T6 (SEQ ID NO:2);

FIG. 7 shows the nucleotide sequence of the 16S rDNA of a bacterial isolate according to the present invention, *Lactobacillus gasseri* C21T1 (SEQ ID NO:3);

FIG. 8 shows the nucleotide sequence of the 16S rDNA of a bacterial isolate according to the present invention, *Lactobacillus gasseri* X21B7 (SEQ ID NO:4);

FIG. 9 shows the nucleotide sequence of the 16S rDNA of a bacterial isolate according to the present invention, *Lactobacillus gasseri* B38T38 (SEQ ID NO:5); and FIG. 10 shows the differences in the 16S rDNA nucleotide sequences amongst the *Lactobacillus acidophilus* B6T7 (SEQ ID NO:6) isolate of the present invention, *L. acidophilus* (SEQ ID NO:7), and *L. plantarum* (SEQ ID NO:8), in which sites of nucleotide differences between the B6T7 isolate and *L. acidophilus* are indicated by the sign " " and sites of nucleotide differences between the B6T7 isolate and *L. plantarum* are indicated by the sign "*".

DETAILED DESCRIPTION OF THE INVENTION

Figure 1:
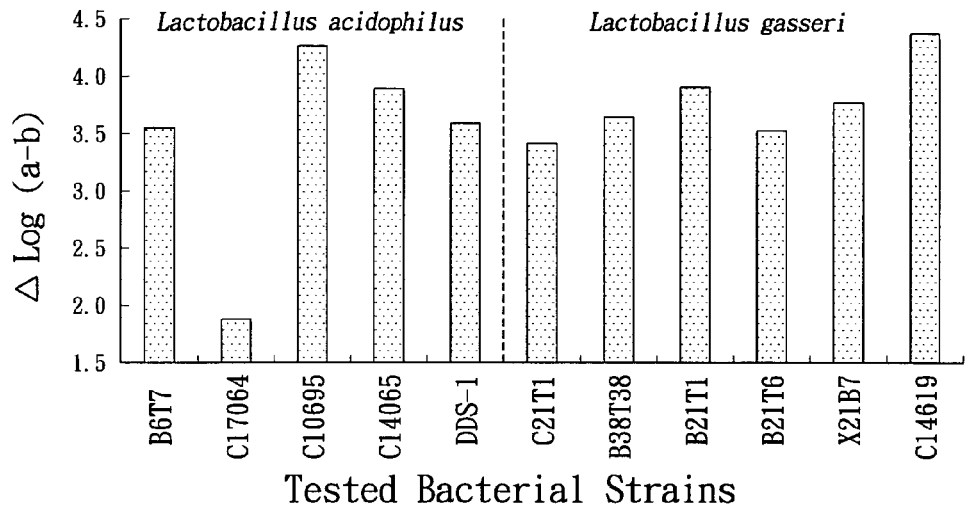
FIG. 1 is a bar diagram showing an acid tolerance comparison between the *Lactobacillus* isolates according to the present invention and known *Lactobacillus* strains, in which the acid tolerance is expressed as Δlog (a-b), wherein "a" stands for the number of viable cells after saline treatment at pH 7 for 2 hours, and "b" stands for the number of viable cells after saline treatment at pH 2 for 2 hours.

In order to obtain *Lactobacillus* strains indigenous to Taiwan and suitable for growth in the gastrointestinal environment of the people of Taiwan, the Applicants used feces of healthy infants aged one to six years living in Hsinchu City, Taiwan as origins for screening desired bacterial strains, and utilized a series of Rogosa agar-based selective media to screen *Lactobacillus*-suspected strains. 400 suspected strains were found in 828 isolates obtained from 43 specimens. These suspected strains were further tested for the characteristics mentioned in the foregoing Summary of the Invention above, which can be summarized as:

1. Stability to acid;
2. Stability to bile salts; and
3. Ability to reduce cholesterol.

These suspected strains were compared with known strains in terms of the aforesaid characteristics, and were screened to obtain 6 *Lactobacillus* isolates having the desired abilities.

The 6 isolates obtained were further identified using the API identification system, Micro-IS System and 16S rDNA sequence analysis. According to the identification results, these 6 isolates were respectively classified and designated as *Lactobacillus gasseri* B21T1, B21T6, C21T1, X21B7 and B38T38, and *L. acidophilus* B6T7. These isolates were deposited in the Food Industry Research and Development Institute (FIRDI, 331 Shih-Pin Road, Hsinchu City 300, Taiwan, R.O.C.) on Jun. 18, 2002, under the Accession Nos. CCRC 910195, CCRC 910196, CCRC 910198, CCRC 910199, CCRC 910197 and CCRC 910194, respectively. These isolates were also deposited in the American Type Culture Collection (ATCC, P.O. Box 1549, Manassas, Va. 20108, USA) under the Budapest Treaty on Jun. 21, 2002, and were given Accession Nos. PTA-4483, PTA-4484, PTA-4479, PTA-4480, PTA-4481 and PTA-4482, respectively.

In view of the beneficial characteristics mentioned above, the *Lactobacillus* isolates according to the present invention are suitable for use as probiotics. For instance, these isolates can be formulated into a broad range of edible materials, including fluid milk (milk, concentrated milk), fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods, nutritional food products, animal feeds, and dietary supplements. The bacterial count in each of these products may be about $10^6$ to $10^9$ CFU (colony forming units) per gram or per milliliter.

It is apparent to those skilled in the art that the *Lactobacillus* isolates of this invention can be used as a food additive component and, according to known methodologies, they may be added during the preparation of raw materials, or, if their participation in fermentation is not desired, they may be added subsequent to the fermentation process, so as to be formulated into forms suitable for ingestion by humans and animals. Preferably, the *Lactobacillus* isolates of the present invention may be formulated into edible materials alone or in combination with at least one other probiotic organism. These probiotic organisms may include *Lactobacillus* sp., such as *L. acidophilus, L. lactis, L. brevis, L. casei, L. plantarum, L. salivatius, L. bifidus, L. bulgadcus, L. causasicus* and *L. rhamnosus; Streptococcus* sp., such as *Streptococcus thermophilus*, and *Streptococcus lactis*; yeasts, such as *Candida Kefyr*, and *Saccharomyces florentinus*; or a combination thereof.

In another application, the *Lactobacillus* isolates of the present invention per se or the above-mentioned products incorporating these isolates are prepared as lyophilized powder or spray dry powder such that each product contains about $10^8$ to more than $10^9$ CFU of active *Lactobacillus* cells. Moreover, such products can be prepared in tablet or capsule form by adding thereto yeast powder, saccharides or other filling agents, e.g. digestion improving drugs or instant foods containing *Lactobacillus*, and bacterial powder for direct consumption.

In addition, the present invention also contemplates the use of the aforesaid *Lactobacillus* isolates alone or in combination with other active ingredients as a medicament in controlling the colonization of undesirable intestinal microorganisms in the alimentary tract of a mammal so as to alleviate gastrointestinal problems caused by these undesirable intestinal microorganisms. The composition of the medicament can be formulated into solution, emulsion, powder, tablet, capsule or other suitable forms for oral administration.

Further, in view of the ability of the *Lactobacillus* isolates of the present invention to reduce cholesterol, it is also contemplated that the *Lactobacillus* isolates of the present invention can be used in the preparation of health food products and non-prescription drugs for reducing serum cholesterol.

As described hereinabove, bacterial strains having bacteriological characteristics identical to those of the *Lactobacillus* isolates of the present invention, their sub-cultured offspring, or mutants derived therefrom are contemplated to fall within the scope and technical concept of the present invention.

As used herein, the term "mutant" refers to a bacterial strain whose genetic composition differs from that of a reference or parent strain by at least one nucleotide due to, e.g. nucleotide substitution, insertion or deletion. A mutant of the invention can be produced by a number of methodologies other than natural mutation. For example, the mutant can be obtained from the random mutagenesis of its parent strain by means of, e.g. chemical mutagen, transposon or irradiation. In addition, a mutant strain of the present invention can include a recombinant nucleic acid sequence. For example, a mutant may be a bacterial strain that harbors an additional nucleic acid sequence, e.g., a sequence transformed, transduced or otherwise inserted into a cell of its parent strain. The additional nucleic acid sequence can encode a polypeptide that is generally or conditionally expressed. Alternatively, the additional nucleic acid sequence can encode a nucleic acid sequence capable of altering cellular physiology, e.g. an anti-sense, a ribozyme, or any other nucleic acid sequence. In another example, the nucleic acid is inserted into an endogenous gene to thereby alter (enhance or destroy) the function of said endogenous gene. For example, the inserted nucleic acid can be a knockout construct that inactivates the endogenous gene, or an artificial enhancer or promoter that increases the transcription of the endogenous gene.

The present invention will be described in more detail with reference to the following examples, which are given for the purpose of illustration only and are not intended to limit the scope of the present invention.

EXAMPLE 1

Isolation and Screening of *Lactobacillus* Isolates

Materials and Methods:

I. Culture Media and Diluents:

1. Screening Culture Media:

(A) Tomato Juice Agar Medium:

| | |
|---|---|
| Casein enzymatic hydrolysate (Sigma, Louis, Mo, USA) | 10 g |
| Skim milk | 10 g |
| Tomato juice | 400 ml |
| Agar | 12 g |
| Distilled water | adjust to 1 L |

(B) Rogosa Agar Medium:

| | |
|---|---|
| Rogosa agar (Merck, Darmstadt, Germany) | 74.5 g |
| Distilled water | 1 L |

After dissolving agar by microwave heating and cooling the resultant mixture to 55° C., adjust pH to 5.5 with acetic acid.

(C) *Lactobacillus* Selective Medium (LBS):

| | |
|---|---|
| Rogosa agar | 8.4 g |
| tomato juice | 40 ml |
| distilled water | 60 ml |

After dissolving agar by microwave heating and cooling the resultant mixture to 55° C., adjust pH to 5.5 with acetic acid.

(D) Rogosa+X-glu agar Medium:

80 mg of 5-bromo4-chloro-3-indolyl-β-D-glucopyranoside (X-glu, Sigma, Louis, Mo., USA) were added in 100 ml of 0.2 M Tris buffer (pH 8.5), and dissolved using sonification. 10 ml of the resultant solution were added to 190 ml of Rogosa agar at 55° C. to form Rogosa+X-glu agar containing X-glu at a final concentration of 40 μg/mL.

2. Bacterial Activation Medium:
(A) Bacto *Lactobacilli* MRS broth (Difco Laboratories, Detroit, Mich., USA); and
(B) MRS agar: Bacto *Lactobacilli* MRS broth supplemented with Agar bacteriological (Scharlau Chemie S. A., Barcelona, Spain)(15 g/L).

3. Ribose Utilization Medium:

Composition of Basal Medium:

| | |
|---|---|
| Bacto proteose peptone no. 3 (Difco Laboratories, Detroit, MI, USA) | 10 g |
| Bacto yeast extract (Difco Laboratories, Detroit, MI, USA) | 5 g |
| Tween 80 | 1 g |
| Ammonium hydrogen citrate | 2 g |
| Sodium acetate | 5 g |
| Magnesium sulfate | 0.1 g |
| Manganese sulfate | 0.05 g |
| Dipotassium (hydrogen) phosphate | 2 g |

-continued

| | |
|---|---|
| Chlorophenol red | 0.05% |
| Distilled water | 1 L |

Adjust pH to 6.3 with HCl.

The basal medium as prepared above was packaged into test tubes in an amount of 4.5 ml basal medium per tube. After being sterilized by autoclaving at 121° C. for 15 minutes, each tube was added with 0.5 ml of a 10% ribose solution that had been sterilized by filtration.

4. Diluent: 0.1% Peptone Water (BACTO Peptone, Difco Laboratories, Detroit, Mich, USA)

II. Procedures to Isolate and Screen *Lactobacillus* Strains:
1. Feces about the size of a finger tip, which were sampled from the middle portion of the feces specimens of infants aged one to six years by using a stick, were added into a test tube containing 9 ml of the above-mentioned diluent (0.1% peptone water) to yield a 10-fold diluted testing solution. The diluted testing solution was stirred sufficiently and uniformly and was then allowed to stand for several minutes so that microorganisms in the specimens were released into the diluent.
2. 1 ml of the aforesaid diluted testing solution was introduced into another test tube containing 9 ml of the same diluent. A serial dilution was conducted in this manner until a $10^4$-fold dilution was made.
3. $10^2$-, $10^3$- and $10^4$-fold diluted testing solutions, each in an amount of 0.2 ml and prepared by the serial dilution described in step 2, were respectively applied to various screening media (Rogosa agar, tomato juice agar, *Lactobacillus* selective medium and Rogosa+X-glu agar) and were spread evenly by using an L-shape glass rod. These screening media were then placed in an anaerobic incubator containing mixed gases (5% $H_2$, 10% $CO_2$ and 85% $N_2$) set at a temperature of 37° C. and cultured for 2 to 4 days;
4. Rod-shaped bacterial colonies, which exhibited blue color on Rogosa+X-glu agar and which were shown to be non-mobile under microscopic examination, or those which appeared semi-transparent when growing on other screening media and which were also non-mobile under microscopic examination, were selected. The bacteria picked up by a stick were introduced into a test tube containing MRS broth and an inner fermentation tube. After culturing at 37° C. for 1 to 2 days, bacterial strains, which proliferated without producing gas and which were shown to have a positive result by Gram-positive staining, were collected.
5. After being activated twice in MRS broth, the bacterial strains collected in step 4 were tested for growth temperature and ribose utilization in the following manners:
    (i) MRS broth medium was inoculated with 1% of a bacterial inoculum and was allowed to stand at 15° C. for 14 days. If the medium showed to have bacteria growth therein, this indicated that the inoculated bacterial strain can grow at 15° C. On the other hand, if no bacteria growth was found on Day 14, this indicated that the inoculated bacterial strain cannot grow at 15° C.
    (ii) MRS broth medium was inoculated with 1% of a bacterial inoculum and was allowed to stand at 45° C. for 2 days. If the medium showed to have bacteria growth therein, this indicated that the inoculated bacterial strain can grow at 45° C. On the other hand, if no bacteria growth was found, this indicated that the inoculated bacterial strain cannot grow at 45° C.
    (iii) A ribose utilization medium was inoculated with 1% of a bacterial inoculum and was allowed to stand at 37° C. for several days.
    (iv) If the color of the culture medium turned from purple to yellow, this indicated that the inoculated bacterial strain is able to utilize ribose for growth and produce acid. If the color of the culture medium remained purple after seven days, the medium was allowed to stand a few more days. If the color of the culture medium still did not turn yellow, this indicated that the inoculated bacterial strain is unable to utilize ribose for growth and produce acid.

III. Results:

In this Example, the *Lactobacillus* screening media were primarily based on Rogosa agar, and some of which were further supplemented with tomato juice or X-glu. Tomato juice is rich in Vitamin B groups and is beneficial to the growth of *Lactobacillus*. As for Rogosa agar, the acetic acid contained therein aids in lowering the pH value so as to inhibit bacterial growth, and the high concentration of acetate ions also has the effect of inhibiting the growth of microorganisms.

When a *Lactobacillus acidophilus* strain is cultured on Rogosa agar, it will form white colonies and it is not easily distinguishable from other strains of *Lactobacillus*. If X-glu is added to Rogosa agar, the bacterial colonies of *Lactobacillus acidophilus* would become blue in color. This is because the cells of *Lactobacillus acidophilus* have the activity of β-D-glucosidase which can break up the β-D-glucosidic bond of X-glu to produce a blue chromogene, which makes the bacterial colonies of *Lactobacillus acidophilus* look blue. However, since this enzyme is also present in the cells of many other microorganisms, the selected bacterial strains have to undergo microscopic examination, Gram staining and the above-mentioned physiological and biochemical tests for ribose utilization and growth temperature before suspected strains with the desired properties can be selected.

Applicants collected 43 feces specimens from healthy infants aged one to six years living in Hsinchu City, Taiwan. The diluted sample of each specimen was plated on each of the selective media according to the procedures described above. When formation of bacterial colony on the selective media was observed, bacterial colonies with different colors and morphologies were selected to undergo microscopic examination. Bacteria colonies which were formed by rod-shaped bacterial calls were further subjected to Gram staining. Any bacteria colony that was found to contain Gram-positive rod bacteria was then selected and referred to as an "isolate."

The isolates thus selected were respectively introduced into MRS broth containing an inner fermentation tube therein, and those that do not produce gas during culture were selected to undergo growth temperature and ribose utilization tests. Any tested strain that can grow at 45° C. but not at 15° C., and that cannot utilize ribose as carbon source for growth would be stowed aside, and the strains selected at this stage are referred to as "suspected strains."

Referring to Table 1, Applicants obtained 400 suspected strains out of a total of 828 isolates selected from the collected 43 specimens.

TABLE 1

Numbering of collected specimens* and numbers of bacterial isolates obtained from said specimens

| Specimen number | Numbers of bacterial isolates | Numbers of suspected strains | Specimen number | Numbers of bacterial isolates | Numbers of suspected strains |
|---|---|---|---|---|---|
| 1 | 40 | 0 | 23 | 3 | 0 |
| 2 | 0 | 0 | 24 | 0 | 0 |
| 3 | 0 | 0 | 25 | 100 | 100 |
| 4 | 26 | 0 | 26 | 0 | 0 |
| 5 | 45 | 0 | 27 | 0 | 0 |
| 6** | 68 | 55 | 28 | 0 | 0 |
| 7 | 0 | 0 | 29 | 0 | 0 |
| 8 | 0 | 0 | 30 | 60 | 0 |
| 9 | 0 | 0 | 31 | 0 | 0 |
| 10 | 0 | 0 | 32 | 0 | 0 |
| 11 | 0 | 0 | 33 | 0 | 0 |
| 12 | 60 | 60 | 34 | 0 | 0 |
| 13 | 0 | 0 | 35 | 0 | 0 |
| 14 | 0 | 0 | 36 | 139 | 115 |
| 15 | 0 | 0 | 37 | 0 | 0 |
| 16 | 0 | 0 | 38** | 120 | 40 |
| 17 | 0 | 0 | 39 | 0 | 0 |
| 18 | 0 | 0 | 40 | 0 | 0 |
| 19 | 0 | 0 | 42 | 60 | 0 |
| 20 | 14 | 0 | 42 | 0 | 0 |
| 21** | 30 | 30 | 43 | 60 | 0 |
| 22 | 3 | 0 | Total | 823 | 400 |

*Origin of specimens: feces from infants aged one to six years living in Hsinchu City, Taiwan.
**The specimen numbers from which the Lactobacillus isolates according to this invention were obtained.

The suspected strains were then subjected to acid tolerance test, bile salt tolerance test and cholesterol lowering test which are described in the following Examples. Six isolates, namely, B21T1, B21T6, C21T1, X21B7, B38T38 and B6T7, exhibited excellent properties in these tests and were therefore compared with the following known bacterial strains in terms of the above-indicated properties:

1. *Lactobacillus acidophilus* CCRC 17064 (corresponding to ATCC 43121; isolated from pigs): this *Lactobacillus* strain has the ability to reduce serum cholesterol (S. E. Gilliland et al. (1985), *Appl. Environ. Microbiol.*, 49: 377-381; S. E. Gilliland and D. K. Walker (1990), *J. Dairy Sci.*, 73:905-911; F. A. M. Kalver and R. van der Meer (1993), *Appl. Environ. Microbiol*, 59: 1120-1124; D. O. Noh et al. (1997), *J. Dairy Sci.*, 82: 3107-3113);

2. *Lactobacillus acidophilus* CCRC 10695$^T$ (corresponding to ATCC 4356; isolated from humans): this *Lactobacillus* strain is a standard strain of *Lactobacillus acidophilus* and is of human origin (D. K. Walker and S. E. Gilliland (1993), *J. Dairy Sci.*, 76:956-961);

3. *Lactobacillus acidophilus* DDS-1 (isolated from humans): this *Lactobacillus* strain is a commercially available product (Nebraska Cultures, Inc.);

4. *Lactobacillus acidophilus* CCRC 14065 [corresponding to CSCO 2401, commercially available from Commonwealth Scientific Industrial Research Organization (CSIRO), Canberra, Australia]; and 5. *Lactobacillus gasseri* CCRC 14619$^T$ (corresponding to ATCC 33323; isolated from humans) (Int. *J. Syst. Bacteriol*. (1980), 30, 601; E. Lauer and O. Kandler, *Bakteriol. Parasitenkd. Infektionskr Hyg. Abt* 1 *Orig.* Reihe C, 1980, 1, 75-78).

EXAMPLE 2

Acid Tolerance Test

I. Experimental Procedures:

The bacterial cell survival test conducted in this example was performed with reference to the method described in J. E. Holcombe et al. (1991), *Cult. Dairy Prod. J.*, 26 (3): 4-5 and that disclosed in U.S. Pat. No. 5,711,977 issued to Y. S. Yang et al., in which a neutral environment (pH 7) and an acidic environment (pH 2) that simulated the stomach were employed.

After being activated twice in MRS broth, the culture of each of the tested bacterial strains was centrifuged at 3,000 rpm for 10 min. After removal of the supernatant, the cell pellet was re-suspended in 1 ml of normal saline (0.85% NaCl, pH 7) and stirred by a stick, followed by vortexing to obtain a homogenous bacterial suspension. Aliquots (0.5 ml) of the resultant bacterial cell suspension were admixed with normal saline solutions of pH 7 and pH 2, respectively, and the resultant mixtures were allowed to stand in a 37° C. incubator for 2 hours. Thereafter, the bacterial cells that survived were counted, and the acid tolerance of each tested bacterial strain was expressed by Δlog (number of bacterial cells), i.e. a calculated log value of (the number of bacterial cells that survived after the normal saline treatment at pH 7 minus the number of bacterial cells that survived after the normal saline treatment at pH 2). Bacterial strains with a smaller value of Δlog (number of bacterial cells) were considered to have higher acid tolerance.

II. Results:

Most microorganisms do not have any tolerance in an acidic environment. Although lactic acid-bacteria per se are acid-producing bacteria, they only grow in environments with pH 3.2 to 4.5. Therefore, the extremely acidic environment of the stomach (pH 2.0 to 3.2) is also a major factor affecting the survival rate of the lactic acid bacteria. Depending on the entry time and type of the gastric contents, the pH value of gastric acid will vary in a range from pH 1.5 to 4.5 during a period of 2 hours in average. Therefore, in the experiment of this example, pH 2 was used as a representative of the gastric pH value. Furthermore, since gastric acid is similar to hydrochloric acid in nature, normal saline with pH adjusted to 2 by hydrochloric acid (0.85% NaCl/ 0.01 N HCl) was used to treat the tested bacterial strains at 37° C. for 2 hours. The bacterial cells that survived in this acid treatment were counted and compared with those of the control group treated with normal saline at pH 7.

The obtained experimental results showed that, after treatments at the above-indicated two different pH values at 37° C. for 2 hours, *Lactobacillus acidophilus* CCRC 17064 exhibited the highest acid tolerance (FIG. 1), and the bacterial count thereof after acid treatment merely decreased by 1.9 in log value. On the other hand, *Lactobacillus acidophilus* CCRC 10695$^T$ and *Lactobacillus gasseri* CCRC $14619^T$ exhibited poor acid tolerance, and their bacterial counts decreased by 4.3 and 4.4 in log value, respectively.

The acid tolerance of the new isolate B21T1 obtained in Example 1 of this invention (which was classified as *Lactobacillus gasseri* according to the bacteriological characteristics thereof, as described in the following Example) is similar to that of CCRC 14065, and their bacterial counts decreased by 3.9 in log value. The other five new isolates of the present invention (B21T6, C21T1, X21B7, B38T38 and B6T7) have similar levels of acid tolerance, and are able to meet the screening index of acid tolerance, a value of Δlog (number of bacterial cells)<4 (U.S. Pat. No. 5,711,977 issued to Y. S. Yang et. al.).

EXAMPLE 3

Bile Salt Tolerance Test

I. Experimental Procedures: 1% of a Bacterial Inoculum

After being activated twice in MRS broth, 1% inoculum of each tested bacterial strain was inoculated into 10 ml MRS broth and 10 mL MRS broth supplemented with 0.3% oxgall (MRSO), respectively. After culturing at 37° C. for 24 hours, the bacterial density ($OD_{660}$) of each culture was measured by a spectrophotometer, and the number of surviving bacterial cells was also counted. The bile salt tolerance is expressed by Δlog (number of bacterial cells), i.e. a calculated log value of (the number of bacterial cells cultured in MRS broth minus the number of bacterial cells cultured in MRSO broth), in which the smaller the calculated Δlog (number of bacterial cells) is, the higher will be the bile salt tolerance of the tested bacterial strain.

II. Results:

Different lactic acid bacteria exhibited vast differences in survival rate after being treated with bile salts. Therefore, screening lactic acid bacteria with bile salt tolerance is important in the selection of probiotic bacteria (S. E. Gilliland et al. (1984), *J. Dairy Sci.*, 67:3045-3051; P. Marteau et al. (1997), *J. Dairy Sci.*, 80:1031-1037). In earlier studies, oxgall was widely used in media for selective culturing of human intestinal bacteria. Therefore, the effectiveness of oxgall should be very similar to that of human bile salts, and oxgall was commonly used in an average concentration of 0.3% (w/v) (S. E. Gilliland and D. K. Walker (1990), *J. Dairy Sci.*, 73: 905-911; D. K. Walker and S. E. Gilliland (1993), *J. Dairy Sci.*, 76: 956-961).

The obtained experimental results showed that, except for $CCRC\ 10695^T$, $CCRC\ 14619^T$ and CCRC 14065, the measured $OD_{660}$ value (bacterial density) of each tested bacterial strain was greater than 2 (Table 2), regardless of whether the tested bacterial strain was cultured in a medium with or without 0.3% oxgall. This indicates that the addition of 0.3% oxgall seems to have little effect upon the growth of the tested bacterial strains.

TABLE 2

Growth comparison of tested bacterial strains cultured in MRS broth with and without 0.3% oxgall for 24 hours.

| Cultures of tested bacterial strains | Bacterial density ($OD_{660}$ value) | |
|---|---|---|
| | MRS Broth | MRS Broth + 0.3% oxgall |
| B6T7 | 2.49 | 2.74 |
| C21T1 | 2.44 | 2.56 |

TABLE 2-continued

Growth comparison of tested bacterial strains cultured in MRS broth with and without 0.3% oxgall for 24 hours.

| Cultures of tested bacterial strains | Bacterial density ($OD_{660}$ value) | |
|---|---|---|
| | MRS Broth | MRS Broth + 0.3% oxgall |
| B38T38 | 2.45 | 2.03 |
| B21T1 | 2.57 | 2.53 |
| B21T6 | 2.62 | 2.29 |
| X21B7 | 2.69 | 2.50 |
| CCRC 17064 | 2.91 | 2.37 |
| $CCRC\ 10695^T$ | 2.35 | 1.09 |
| CCRC 14065 | 2.55 | 1.79 |
| $CCRC\ 14619^T$ | 2.96 | 1.58 |
| DDS-1 | 2.87 | 2.72 |

However, it is also noted that the bacterial densities of two new isolates according to the present invention, namely, B6T7 and C21T1, are higher in MRSO broth than in MRS broth. This shows that other factors may exist that interfere with light absorption. Therefore, the numbers of surviving bacterial cells of the tested bacterial strains cultured in these two media for 24 hours were further examined.

Figure 2:
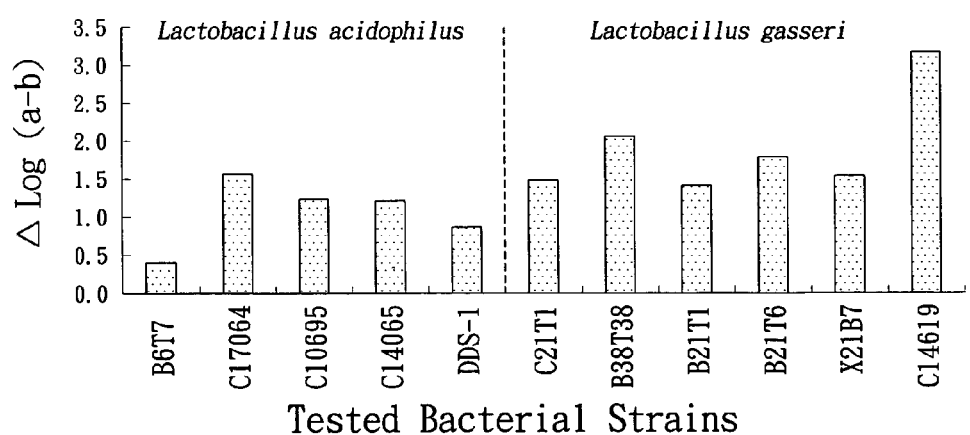
FIG. 2 is a bar diagram showing a bile salt tolerance comparison between the *Lactobacillus* isolates according to the present invention and known *Lactobacillus* strains, in which the bile salt tolerance is expressed as Δlog (c-d), wherein "c" stands for the number of viable cells after incubation in MRS broth for 24 hours, and "d" stands for the number of viable cells after incubation in MRS broth supplemented with 0.3% oxgall for 24 hours.

Referring to FIG. 2, it can be seen from a reduction in the cell number of bacterial strains examined that, $CCRC\ 14619^T$ has a very poor bile salt tolerance, and $CCRC\ 10695^T$ and the new isolate B38T38 of the present invention were shown to have a bile salt tolerance higher than that of $CCRC\ 14619^T$, respectively. The bacterial strain exhibiting the highest bile salt tolerance is the new isolate B6T7 of the present invention, and the bile salt tolerance of the rest of the bacterial strains being substantially similar. That is, after culturing for 24 hours in MRS broth containing 0.3% oxgall, the numbers of dead bacterial cells thereof range from 1 to 2 in log values.

Figure 3:
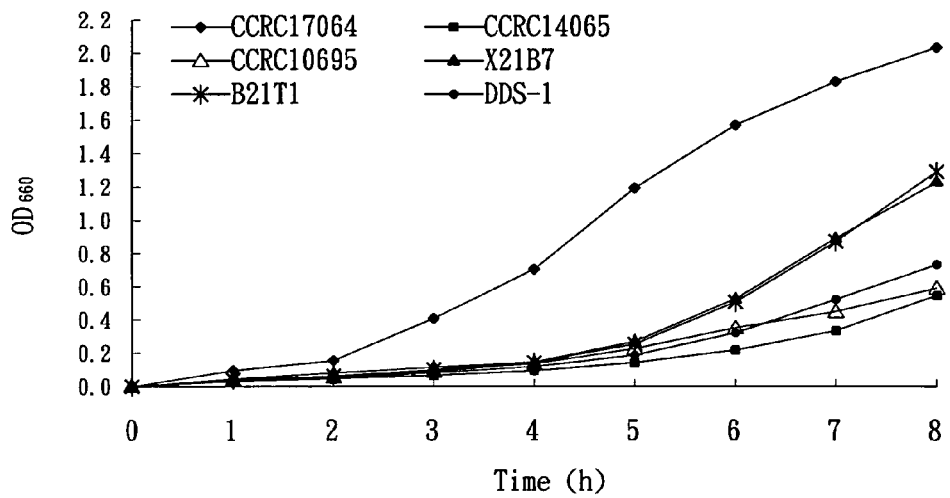
FIG. 3 is a bar diagram showing a growth comparison between the *Lactobacillus* isolate according to the present invention and known *Lactobacillus* strains, both of which were grown in MRS broths with 0.3% oxgall.

Further, the growth curves of some bacterial strains cultured in MRS broth containing 0.3% oxgall were observed. The growth rate of each of the tested strains is represented by the gradient of the growth curve. That is to say, the larger the gradient, the faster the growth rate, and thus, the higher the tolerance to bile salt. It can be seen from FIG. 3 that the growth rate of CCRC 17064 is the fastest, those of the new isolates X21B7 and B21T1 of the present invention being slower, and those of CCRC 14065, $CCRC\ 10695^T$ and DDS-1 being the slowest.

Although slight differences are present amongst the experimental results obtained from different observation methods, it can be appreciated from these tests that the six new *Lactobacillus* isolates screened in the present invention exhibit same tolerance against acid and bile salts.

EXAMPLE 4

Assay for the Ability of the Tested Bacterial Strains in Lowering Cholesterol

Figure 4:
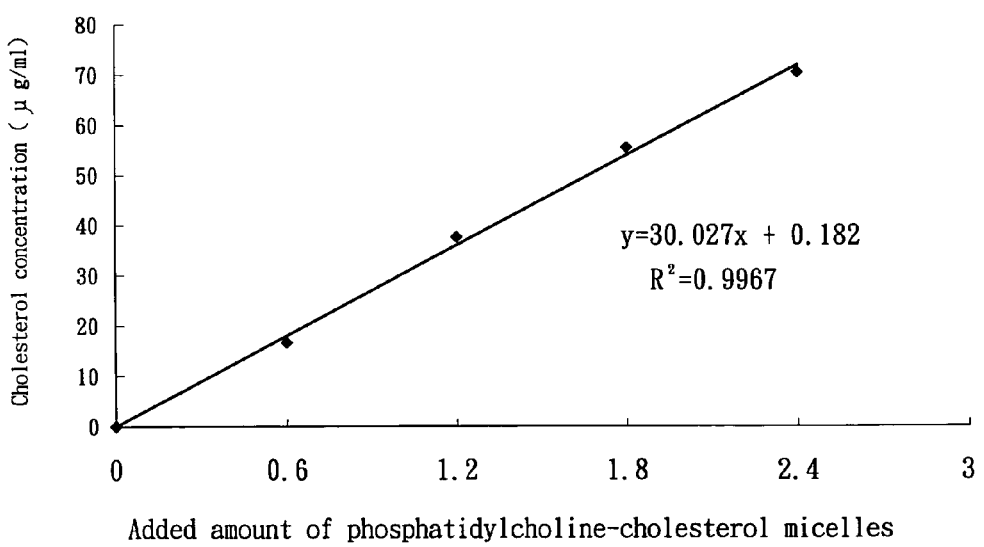
FIG. 4 shows the relationship between the concentration of cholesterol and the amount of phosphatidycholine-cholesterol micelles, said micelles being prepared with reference to S. Razin et al. (1980), *Biochimica Biophysica Acta*, 598:628-640, for the purpose of testing the cholesterol-lowering ability of the isolated bacterial strains according to the present invention.

I. Experimental Procedure:

(A) Source of Cholesterol:

In respect to the test of bacterial strains in lowering cholesterol, PPLO (BACT PPLO SERUM FRACTION) was used as the source of cholesterol in most prior references and patent publications. However, production of this product has already ceased. Therefore, in this Example, Applicants adopted the phosphatidycholine-cholesterol preparation methods disclosed in Huang, C. and T. E. Thomopson (1974), *Methods Enzymol.*, 32:485-489 and in S. Razin et al. (1980), *Biochimica Biophysica Acta*, 598: 628-640, in which horse serum and phosphatidycholine-cholesterol were used as the source of cholesterol to prepare a homogeneously distributed phosphatidycholine-cholesterol solution, the volume of which is in a positive linear functional relationship with the cholesterol concentration (FIG. 4).

1. Horse serum

Horse serum dissolved in water was filtered through a 0.45 µm membrane filter and was stored in a −20° C. refrigerator.

2. Phosphatidycholine-cholesterol (egg lecithin+cholesterol)

According to S. Razin et al. (1980), *Biochimica Biophysica Acta*, 598:628-640, egg Lecithin and cholesterol were placed into a ground stopper bottle of a rotary vacuum evaporator (EYELA), and were uniformly dissolved in a sufficient amount of chloroform, followed by drying via nitrogen purging so that cholesterol and egg lecithin were mixed homogeneously to form a uniform film on the glass wall of the ground stopper bottle. After re-dissolving the film in a 0.4 M sucrose solution, the ground stopper bottle was charged with $N_2$ gas therein and then sealed with a cap, followed by wrapping with an aluminum foil, so as to reduce the probability of lipid oxidization.

After the sealed ground stopper bottle was sonicated in a water bath-type sonicator at 4° C. for 15 minutes, the mixed solution thus formed was passed through a 0.22 µm membrane filter under pressure twice, and was then stored in a 4° C. refrigerator (the solution must be used within 3 days of its preparation).

(B) Test Grouping:

Test (1): After being activated twice in MRS broth, 1% inoculum of each of the tested bacterial strains was inoculated into 10 ml MRSS containing 8.8 ml MRS, 1.2 ml cholesterol solution as prepared above and 0.3% oxgall, and cultured in a 37° C. anaerobic incubator (10% $CO_2$ and 90% $N_2$) for 24 hours. Thereafter, according to the method described in Item (C) below, supernatant samples and cell pellet samples were respectively collected from the resultant cultures inoculated with the tested bacterial strains for measurement of cholesterol content.

Test (2): After being activated twice in MRS broth, 1% inoculum of each of the tested bacterial strains was inoculated into 10 mL MRSO and cultured at 37° C. for 20-22 hours. Thereafter, 1% inoculum taken from the resultant culture of each tested bacterial strain was inoculated into 10 ml MRSS and cultured in a 37° C. anaerobic incubator (10% $CO_2$ and 90% $N_2$) for 24 hours. Thereafter, according to the method described in Item (C) below, supernatant samples and cell pellet samples were respectively collected from the resultant cultures inoculated with the tested bacterial strains for measurement of cholesterol content.

(C) Measurement of Cholesterol Content

The measurement of cholesterol content was conducted according to the o-phthalaldehyde method (L. L. Rudel and M. D. Morris (1973), Notes on *Methodology*, 14:364-366; S. E. Gilliland et al. (1985), *Appl. Environ. Microbiol*, 49: 377-381).

With respect to each of the resultant cultures inoculated with the tested bacterial strains as described in the above Test (1) and Test (2), a tested bacterial solution in an amount of 1 ml was sampled and centrifuged at 12,000 rpm for 10 minutes. 0.5 ml of the supernatant thus formed was placed into a tube to serve as a supernatant specimen of the resultant culture inoculated with a respective tested bacterial strain.

With respect to each of the resultant cultures inoculated with the tested bacterial strains as described in the above Test (1) and Test (2), a tested bacterial solution in an amount of 1 ml was sampled and centrifuged at 3,000 rpm for 10 minutes, and the resultant supernatant was removed. The left cell-pellet was re-dissolved in 10 ml MRSO broth and mixed uniformly. A 0.5 ml solution was taken from the resultant mixture and placed into a test tube to serve as a cell-pellet specimen of the resultant culture inoculated with a respective tested bacterial strain.

Each tested specimen was added with 3 ml of 95% ethanol and mixed well by uniform shaking. 2 ml of 50% KOH was further added thereto, and the resultant mixture was again shaken uniformly. Thereafter, the mixture was heated at 60° C. in a water bath for 10 minutes and then allowed to cooled at room temperature. The cooled mixture was added with 5 ml hexane and stirred uniformly, followed by addition of 3 ml $H_2O$. After being shaken uniformly, the mixture so formed was allowed to stand at room temperature for 15 minutes. 2.7 ml of the resultant hexane layer was removed into another test tube, and hexane was evaporated at 60° C. under $N_2$. The solid residue left after evaporation was added with 4 ml of a o-phthalaldehyde reagent solution (0.5 mg o-phthalaldehyde/1 ml acetic acid). The resultant mixture was shaken uniformly and allowed to stand at room temperature for 10 minutes, followed by addition of 2 ml concentrated sulfuric acid. The mixture thus formed was shaken uniformly and allowed to stand at room temperature for 10 minutes. Thereafter, the mixture was subjected to an $OD_{550}$ measurement using a spectrophotometer.

(D) Assessment of the Ability of a Tested Bacterial Strain in Lowering Cholesterol The ability of a bacterial strain in lowering cholesterol was estimated using the following formula:

$$A = 100 - [(B/C) \times 100]$$

A=reduction in cholesterol (%)

B=cholesterol content (mg) in the supernatant of the culture inoculated with the tested bacterial strain C=cholesterol content (mg) in the supernatant of the culture without inoculation of the tested bacterial strain (control group)

If the value of "A" value is greater than 80%, the bacterial strain is considered to have a notable ability in lowering cholesterol.

(E) Assessment of the Ability of a Tested Bacterial Strain in Assimilating Cholesterol $$A'=100-[(B'+C')\times100]$$

A'=assimilation of cholesterol (%)
B'=cholesterol content (mg) in the supernatant of the culture inoculated with the tested bacterial strain
C'=cholesterol content (mg) in the cell-pellet of the culture inoculated with the tested bacterial strain If the value of "A'" value is greater than 15%, the bacterial strain is considered to have a notable ability in assimilating cholesterol.

II. Result:

(i) The Abilities of Tested Bacterial Strains in Lowering Cholesterol

In comparing Test (1) (i.e. culturing a tested bacterial strain in MRS broth) and those of Test (2) (i.e. culturing a tested bacterial strain in MRSO broth), the difference therebetween resides in that in Test (2), a tested bacterial strain was inoculated into MRSO broth and cultured for 20 to 22 hours. 1% inoculum was taken therefrom and inoculated into 10 ml MRSS for further culture. The purpose of Test (2) is to screen the tested bacterial strains again to determine whether they have excellent bile salt tolerance, and to also screen bacterial strains having the ability in lowering cholesterol.

The results of the tests using horse serum as cholesterol source (Table 3) showed that prior *Lactobacillus acidophilus* CCRC 17064 and DDS-1 also demonstrated significant effects in this test, and their abilities in lowering cholesterol reached 88 to 98%. On the other hand, the abilities of CCRC 14065, CCRC 10695$^T$ and CCRC 14619$^T$ in lowering cholesterol were not significant. This might be due to the fact that these bacterial strains have poor bile salt tolerance and do not grow well in MRSO broth so that their cholesterol lowering abilities as observed reached only 30 to 43%.

In these two tests, the new isolates of the present invention, i.e. B6T7, C21T1, B21T1, B21T6, B38T38 and X21B7, were shown to have a cholesterol lowering ability up to 91-99% or more, which is slightly higher than those of CCRC 17064 and DDS-1. This shows that the bacterial strains screened in accordance with the present invention also have excellent ability in lowering serum cholesterol.

TABLE 3

Assessment of the ability of tested bacterial strains in decreasing cholesterol (horse serum model)[a]

| Cultures | Growth in MRS broth[b] | | Growth in MRSO broth[c] | |
| --- | --- | --- | --- | --- |
| | Cholesterol[d] in spent broth (μg/ml) | Cholesterol decrease (%) | Cholesterol[d] in spent broth (μg/ml) | Cholesterol decrease (%) |
| B6T7 | 6.71 | 92.2 | 7.14 | 92.7 |
| C21T1 | 0.69 | 99.2 | 2.41 | 97.2 |
| B38T38 | 2.24 | 97.4 | 7.57 | 91.2 |
| B21T1 | 3.10 | 96.6 | 0.34 | 99.6 |
| B21T6 | 2.84 | 96.7 | 2.24 | 97.4 |
| X21B7 | 1.34 | 98.4 | 3.27 | 96.2 |
| CCRC 17064 | 1.12 | 98.7 | 9.81 | 88.4 |
| CCRC 10695 | 8.00 | 90.7 | 56.97 | 33.8 |
| CCRC 14065 | 11.70 | 86.4 | 59.90 | 30.4 |
| CCRC 14619 | 2.84 | 96.7 | 49.14 | 42.9 |
| DDS-1 | 5.94 | 93.1 | 5.16 | 94.0 |
| Control | 86.06 | — | 86.06 | — |

[a]MRS broth supplemented with 0.3% oxgall and 12% horse serum.
[b]Before the test, all cultures were sub-cultured in MRS broth using 1% inoculum and incubated at 37° C. for 24 h.
[c]Before the test, all cultures were sub-cultured in MRSO broth (MRS broth with 0.3% oxgall) using 1% inoculum and incubated at 37° C. for 24 h.
[d]Initial cholesterol content in broth was 86.06 μg/ml.

Referring to Table 4, when phosphatidycholine-cholesterol was used instead of horse serum as cholesterol source in the test in connection with the assessment of the ability of tested bacterial strains in lowering cholesterol, it was observed that the ability of each bacterial strain in terms of cholesterol decrease (%) tends to decrease. This indicates that the ability of *Lactobacillus* strains in lowering cholesterol level may vary with the type of cholesterol in use. It is noted that the ability of CCRC 17064 in lowering phosphatidycholine-cholesterol is 11 to 29%, whereas the abilities of the bacterial strains of the present invention in lowering phosphatidycholine-cholesterol reached 23 to 48%, which is evidently higher than that achieved by CCRC 17064, although slightly lower than that achieved by DDS-1 (50%).

TABLE 4

Assessment of the abilities of tested bacterial strains in lowering cholesterol (phosphatidylcholine-cholesterol micelle model)[a]

| Cultures | Growth in MRS broth[b] | | Growth in MRSO broth[c] | |
| --- | --- | --- | --- | --- |
| | Cholesterol[d] (μg/ml) | Cholesterol decrease (%) | Cholesterol[d] (μg/ml) | Cholesterol decrease (%) |
| B6T7 | 45.05 | 23.92 | 33.70 | 43.10 |
| C21T1 | 30.71 | 48.15 | 43.59 | 26.40 |
| B38T38 | 33.75 | 43.01 | 35.16 | 40.62 |
| B21T1 | 32.34 | 45.39 | 32.83 | 44.57 |
| B21T6 | 35.43 | 40.16 | 36.25 | 38.79 |
| X21B7 | 35.11 | 40.71 | 39.29 | 33.65 |
| CCRC 17064 | 52.66 | 11.07 | 42.01 | 29.06 |
| DDS-1 | 29.24 | 50.63 | 29.46 | 50.26 |
| Control | 59.22 | — | 59.22 | — |

[a]MRS broth supplemented with 0.3% oxgall and 12% phosphatidylcholine-cholesterol micelles.
[b]Before the test, all cultures were sub-cultured in MRS broth using 1% inoculum and incubated at 37° C. for 24 h.
[c]Before the test, all cultures were sub-cultured in MRSO broth (MRS broth with 0.3% oxgall) using 1% inoculum and incubated at 37° C. for 24 h.
[d]Initial cholesterol content in broth was 59.22 μg/ml.

(ii) Cholesterol Assimilation by Tested Bacterial Strains:

Concerning the mechanism of lactic acid bacteria in lowering cholesterol, cholesterol is removed by the co-precipitation of cholesterol and deconjugated bile salts (F. A. M. Kalver and R. van der Meer (1993), supra, M. M. Brashears and S. E. Gililland (1997), supra), and the assimilation of cholesterol by the bacterial strain per se (Gilliland et al. (1985), supra; D. O. Noh et al. (1997), supra; and Zhang et al (1998), supra).

Referring to Table 5, it can be seen that CCRC 17064, the six isolates obtained according to the present invention, and DDS-1 can assimilate cholesterol. However, different bacterial strains differ slightly in their abilities to assimilate cholesterol. The observed assimilation rate is in the range of from 11 to 40%. Cholesterol assimilation by CCRC 14065, CCRC 10695$^T$ and CCRC 14619$^T$ was not significant.

H. A., Mair, N. S., Sharpe, M. E., and Hotl, J. G., ed.) Vol. II. pp. 1208-1234. The Williams & Wilkins Co., Baltimore, USA).

(2) API Identification System:

This identification test is based on that described in G. H. Fleet et al. (1984), *Appl. Environ. Microbiol.*, 48: 1034-1038. The identity of the lactic acid bacteria was verified with the API 50 CHL Kit (French API BioMerieux Research Laboratory, La Balme Les Grottes, Montalien, Jeraeh, France). The items tested were: tests of acid production from 49 carbon sources that include: glycerin, erythritol, D-arabinose, L-arabinose, ribose, D-xylose, L-xylose, adonitol, β-methyl-xyloside, galactose, D-glucose, D-fructose, D-mannose, L-sorbose, rhamnose, dulcitol, inositol, mannitol, sorbitol, α-methyl-D-mannoside, α-methyl-D-gluco-

TABLE 5

Assessment of the cholesterol assimilation[a] of tested bacterial strains

| | Growth in MRS broth[b] | | | Growth in MRSO broth[c] | | |
|---|---|---|---|---|---|---|
| Cultures | Cholesterol[d] in spent broth (%) | Cholesterol in cell pellet (%) | Cholesterol assimilated (%) | Cholesterol[d] in spent broth (%) | Cholesterol in cell pellet (%) | Cholesterol assimilated (%) |
| B6T7 | 7.8 | 51.4 | 40.8 | 7.3 | 74.1 | 18.6 |
| C21T1 | 0.8 | 86.0 | 13.2 | 2.8 | 72.3 | 24.9 |
| B38T38 | 2.6 | 79.1 | 18.3 | 8.8 | 83.7 | 7.5 |
| B21T1 | 3.4 | 81.7 | 14.9 | 0.4 | 88.4 | 11.2 |
| B21T6 | 3.3 | 67.2 | 29.5 | 2.6 | 81.4 | 16.0 |
| X21B7 | 1.6 | 67.0 | 31.4 | 3.8 | 71.3 | 24.9 |
| CCRC 17064 | 1.3 | 68.5 | 30.2 | 11.6 | 72.9 | 15.5 |
| CCRC 10695 | 9.3 | 71.7 | 19.0 | 66.2 | 33.4 | 0.4 |
| CCRC 14065 | 13.6 | 82.0 | 4.4 | 69.6 | 27.8 | 2.6 |
| CCRC 14619 | 3.3 | 80.6 | 16.1 | 57.1 | 42.7 | 0.2 |
| DDS-1 | 6.9 | 78.5 | 14.6 | 6.0 | 81.3 | 11.2 |

[a]MRS broth supplemented with 0.3% oxgall and 12% horse serum.
[b]Before the test, all cultures were sub-cultured in MRS broth using 1% inoculum and incubated at 37° C. for 24 h.
[c]Before the test, all cultures were sub-cultured in MRSO broth (MRS broth with 0.3% oxgall) using 1% inoculum and incubated at 37° C. for 24 h.
[d]The concentration of cholesterol in the control was defined as 100 parts.

Summarizing the above test results, it is clear that the six new *Lactobacillus* isolates, obtained and screened in Taiwan in accordance with the present invention, have demonstrated excellent acid- and bile salt-resistance and the ability to lower cholesterol. Further identification and characterization tests of these *Lactobacillus* isolates were conducted in the following examples.

EXAMPLE 5

Identification and Characterization of *Lactobacillus* Isolates

I. Experimental Procedures:

(1) Preliminary Identification Tests:

Freshly cultured bacterial strains (cultured for 18 to 24 hours) were subjected to preliminary identification tests, the conducted items of which include: Gram staining, morphological observations, catalase test, motility, growth under aerobic and anaerobic conditions (O. Kandler and N. Weiss (1986), Regular, nonsporing Gram-positive rods and Cocci. In: Bergey's Manual of Systematic Bacteriology. (Sneath, P.

side, N-acetyl glucosamine, amygdalin, arbutine, esculin, salicin, cellobiose, maltose, lactose, melibiose, saccharose, trehalose, inuline, melezitose, D-raffinose, amidon, glycogen, xylitol, β-gentiobiose, D-turanose, D-lyxose, D-tagatose, D-fucose, L-fucose, D-arabitol, L-arabitol, gluconate, 2-keto-gluconate, and 5-keto-gluconate.

The API system works according to the following operating procedures: using a sterile swab to pick up a bacterial colony grown on a culture plate and allowing the picked bacterial colony to be evenly suspended in 2 ml of 0.85% normal saline; sucking the bacterial cell-suspended solution using a sterile pipette and dropping n-drops of the solution into another 5 ml of 0.85% sterile normal saline such that the concentration of the resultant bacterial solution is equivalent to that of McFarland No. 2 standard solution (a mixed solution formed from 9.8 ml of 1% $H_2SO_4$ and 0.2 ml of 1% $BaCl_2$). In the meantime, an additional bacterial cell-suspended solution is taken, and 2 n drops of the solution are pipetted into a glass tube containing API 50 CHL medium. After mixing uniformly, a proper volume of the inoculum so prepared is added into each of the tubes of a test strip, overlaid with mineral oil, and placed in the incubation tray (adding water to the tray beforehand so as to avoid loss of the medium through evaporation during incubation). After being covered with an incubation lid, the incubation tray is allowed to stand at 37° C. for 48 hours and is subsequently taken out for reading purposes. The results are recorded and compared with the database of API LAB Software identification system, so as to determine the most appropriate taxonomic genera and species for the bacterial colony under test.

(3) Micro-IS System:

The Micro-IS System is based on the method proposed by M. Rogosa et al (1971), Method for coding data on microbial strains for computers (edition AB), Int. J. Syst. Bacteriol. 21:1A-184A, and utilizes Matrix 5 of Micro-IS System (suitable for *Lactobacillus* sp.). The test items include: motility; growth temperature test (15° C., 45° C.); growth under aerobic conditions; tests of gas production from D-glucose and glucose; tests of acid production from amygdalin, L-arabinose, cellobiose, D-fructose, D-galactose, D-glucose, lactose, maltose, D-mannitol, D-mannose, melezitose, melibiose, rhamnose, L-rhamnose, D-ribose, salicin, D-sorbitol, sucrose, trehalose and D-xylose; and growth tests in terms of esculin hydrolysis and L-arginine deamination. The positive or negative result of each test is inputted into the Micro-IS computer identification program to yield the taxonomic genus or species of the identified bacteria.

(4)16S rDNA Sequence Analysis:

This identification test is based on the method described in Rosenblum et al. (1997), *Nucleic Acid Res.,* 25: 4500-4504, and it works according to the following operating procedures: A small amount of a freshly cultured bacterial strain is scraped and placed into a 1.5 ml eppendorf tube. After treating the bacterial sample with proteinase K and RNase and using a spin column to obtain the bacterial genomic DNA therefrom, PCR amplification is conducted, followed by purification. After confirmation by electrophoresis, the PCR-amplified products are subjected to reaction with a MICROSEQ 16S rDNA Gene Kit (PE Co., USA), followed by DNA sequencing using the ABI Prism 310 Genetic Analyzer. Furthermore, the 12 strips of DNA sequences thus obtained are analyzed and integrated by using MICROSEQ software (PE Co., USA) to obtain a 16S rDNA sequence of about 1500 bps, said sequence being subjected to a comparison with DNA databases (MICROSEQ Reference Manual, 1999, PE CO., USA).

II. Results:

1. Isolate B21T1 of the Present Invention
   (i) According to the results of preliminary identification test, the isolate B21T1 is gram-positive, catalase negative and non-mobile, and it grows under both aerobic and anaerobic conditions;
   (ii) The test results using API 50 CHL identification kit of API System are shown in Table 6, in which the identification score is 91.0 (% ID). The identity of this isolate is confirmed to be *Lactobacillus acidophilus;*
   (iii) The isolate B21T1 of the present invention is identified as *Lactobacillus acidophilus* by the Micro-IS System, in which the obtained results are shown in Table 7 and the identification score is 0.682 (ID score);
   (iv) The 16S rDNA sequence analysis result of the isolate B21T1 of the present invention is shown in FIG. 5. After a comparison with DNA databases (MICROSEQ Reference Manual, 1999, PE CO., USA), it was found that the 16S rDNA sequence (SEQ ID NO:1) of the isolate B21T1 of the present invention is most homologous to the 16S rDNA sequence of *Lactobacillus gasseri* ($B_1$ group in *Lactobacillus acidophilus*) (G. Klein et al. (1998), *International Journal of Food Microbiology.* 41:103-125); and
   (v) According to the above-mentioned identification results, the isolate B21T1 of the present invention is most probably *Lactobacillus gasseri,* subgroup $B_1$ of *Lactobacillus acidophilus.*

TABLE 6

```
Reference: B2IT1
DOUBTFUL PROFILE

Strip: API 50 CHL
Profile: ---------- -+-+?----- --++-++++- -+-------+ ----------
  0   - GLY - ERY - DARA - LARL - RIB - DXYL - LXYL - ADO - MDX - GAL -
  GLU + FRU - MNE + SBE ? RHA - DUL - INO - MAN - SOR - MDM - MDG -
  NAG + AMY - ARB - ESC + SAL + CEL + MAL + LAC - MEL - SAC + TRE -
  INU - MLZ - RAF - AMD - GLYG - XLT - GEN + TUR - LYX - TAG - DFUC -
  LFUC - DARL - LARL - GNT - 2KG - 5KG -
```

| Significant taxa | | % Id. | T | Tests against |
|---|---|---|---|---|
| Lacto. acidophilus | 1 | 91.0 | 0.53 | 3 |
| Next choice | | | | |
| Lacto. crispatus | 2 | 5.4 | 0.35 | 4 |
| Lacto. acidophilus | | 1:3 test(s) against | | |
| GALACTOSE | (GAL) | 75% | D-FRUCTOSE | (FRU) 100% |
| TREHALOSE | (TRE) | 77% | | |

TABLE 7

Micro-IS System
Strain names: B21T1, B21T6, C21T1, X21B7, B6T7

| | | | | |
|---|---|---|---|---|
| − | 013001 | MOTILITY | − 006001 | ENDOSPORES |
| − | 017013 | GROWTH 15° C. | + 017017 | GROWTH 45° C. |
| + | 016059 | AEROBIC GROWTH | − 024045 | GLUCOSE TO $CO_2$ |

TABLE 7-continued

Micro-IS System
Strain names: B21T1, B21T6, C21T1, X21B7, B6T7

| | | | | | |
|---|---|---|---|---|---|
| − | 028528 | GLUCONATE, GAS | + | 025203 | AMYGDALIN, ACID |
| − | 025181 | L-ARABINOSE, ACID | + | 025211 | CELLOBIOSE, ACID |
| + | 025193 | D-FRUCTOSE, ACID | + | 025194 | D-GALACTOSE, ACID |
| + | 025195 | D-GLUCOSE, ACID | + | 025212 | LACTOSE, ACID |
| + | 025213 | MALTOSE, ACID | − | 026371 | D-MANNITOL, ACID |
| + | 025196 | D-MANNOSE, ACID | − | 025217 | MELEZITOSE, ACID |
| + | 025214 | MELIBIOSE, ACID | + | 025218 | RAFFINOSE, ACID |
| − | 025191 | L-RHAMNOSE, ACID | − | 025184 | D-RIBOSE, ACID |
| + | 025210 | SALICIN, ACID | − | 026374 | D-SORBITOL, ACID |
| + | 025215 | SUCROSE, ACID | + | 025216 | TREHALOSE, ACID |
| − | 025186 | D-XYLOSE, ACID | + | 028060 | L-MALATE UTIL |

| *DIAGNOSIS* | **ID SCORE | **LIEKLIHOOD | **BESTLIKEL. |
|---|---|---|---|
| 1 L. acidophilus | 0.68224 | 0.079110108 | 0.0791101 |
| 2 L. vitulinus | 0.31761 | 0.036828671 | 0.1104860 |

| SUGGESTED TESTS | VALUE IN SETVALUE ALONE |
|---|---|
| 1 024029 (L+) LACTATE PROD | 1 |

2. Isolate B21T6 of the Present Invention (i) According to the preliminary identification results, the isolate B21T6 is gram-positive, catalase negative and non-mobile, and it grows in both aerobic and anaerobic conditions;

(ii) The test results using API 50 CHL identification kit of the API System are shown in Table 8, in which the identification score is 93.6 (% ID). The identity of this isolate is confirmed to be *Lactobacillus acidophilus;*

(iii) The isolate B21T6 of the present invention is identified to be *Lactobacillus acidophilus* by the Micro-IS System, in which the obtained results are shown in Table 7, and the identification score is 0.682 (ID score);

(iv) The 16S rDNA sequence analysis result of the isolate B21T6 of the present invention is shown in FIG. 6. After a comparison with DNA databases (MICROSEQ Reference Manual, 1999, PE CO., USA), it was found that the 16S rDNA sequence (SEQ ID NO:2) of the isolate B21T6 of the present invention is most homologous to the 16S rDNA sequence of *Lactobacillus gasseri* ($B_1$ group in *Lactobacillus acidophilus*); and (v) According to the above-mentioned identification results, the isolate B21T6 of the present invention is most probably *Lactobacillus gasseri*, subgroup $B_1$ of *Lactobacillus acidophilus*.

TABLE 8

```
Reference: B21T6
VERY GOOD IDENTIFICATION TO THE GENUS

Strip: API 50 CHL
Profile: ---------- -++------- --+--+++-- -+-------- ----------
   0  - GLY  - ERY  - DARA - LARL - RIB - DXYL - LXYL - ADO - MDX -  GAL  -
  GLU + FRU  + MNE  - SBE  - RHA - DUL  - INO  - MAN - SOR - MDM -  MDG  -
  NAG + AMY  + ARB  - ESC  + SAL + GEL + MAL  + LAC - MEL - SAC +  TRE  -
  INU - MLZ  - RAE  - AMD  - GLYG - XLT - GEN  + TUR - LYX - TAG -  DFUC -
  LFUC - DARL - LARL - GNT  - 2KG  - 5KG -
```

| Significant taxa | | % Id. | T | Tests against |
|---|---|---|---|---|
| Lacto. acidophilus | 3 | 93.6 | 0.80 | 1 |
| Lacto. delb.delb. | | 6.0 | 0.65 | 5 |
| Next choice | | | | |
| Lacto. crispatus | | 0.2 | 0.39 | 4 |

| Lacto. acidophilus | 1:1 test(s) against |
|---|---|
| D-MALTOSE (MAL) | 75% |

3. Isolate C21T1 of the Present Invention (i) According to the preliminary identification results, the isolate C21T1 is gram-positive, catalase negative and non-mobile, and it grows under aerobic and anaerobic conditions;

(ii) The test results using API 50 CHL identification kit of the API System are shown in Table 9, in which the identification score is 95.6 (% ID). The identity of this isolate is confirmed to be *Lactobacillus acidophilus;*

(iii) The isolate C21T1 of the present invention is identified to be *Lactobacillus acidophilus* by the Micro-IS System, in which the obtained results are shown in Table 7, and the identification score is 0.682 (ID score);

(iv) The 16S rDNA sequence analysis result of the isolate C21T1 of the present invention is shown in FIG. 7. After a comparison with DNA databases (MICROSEQ Reference Manual, 1999, PE CO., USA), it was found that the 16S rDNA sequence (SEQ ID NO:3) of the isolate C21T1 of the present invention is most homologous to the 16S rDNA sequence of *Lactobacillus gasseri* ($B_1$ group in *Lactobacillus acidophilus*); and (v) According to the above-mentioned identification results, the isolate C21T1 of the present invention is most probably *Lactobacillus gasseri*, subgroup $B_1$ of *Lactobacillus acidophilus.*

TABLE 9

Reference: C21T1
GOOD IDENTIFICATION

Strip: API 50 CHL
Profile: ---------- -++------- --++-++++- -+-------+ ----------
    0   - GLY - ERY - DARA - LARL - RIB - DXYL - LXYL - ADO - MDX - GAL -

GLU + FRU + MNE - SBE - RHA - DUL - INO - MAN - SOR - MDM - MDG -

NAG + AMY + ARB - ESC + SAL + GEL + MAL + LAC - MEL - SAC + TRE -

INU - MLZ - RAE - AMD - GLYG - XLT - GEN + TUR - LYX - TAG - DFUC -

LFUC - DARL - LARL - GNT - 2KG - 5KG -

| Significant taxa | | % Id. | T | Tests against |
|---|---|---|---|---|
| Lacto. acidophilus | 1 | 95.6 | 0.70 | 3 |
| Next choice | | | | |
| Lacto. crispatus | | 1.5 | 0.53 | 5 |

| Lacto. acidophilus | | 1:3 test(s) against | | |
|---|---|---|---|---|
| GALACTOSE | (GAL) | 75% | D-MANNOSE | (MNE) 96% |
| TREHALOSE | (TRE) | 77% | | |

4. Isolate X21B7 of the Present Invention
(i) According to the preliminary identification results, the isolate X21B7 is gram-positive, catalase negative and non-mobile, and it grows under both aerobic and anaerobic conditions;
(ii) The test results using API 50 CHL identification kit of the API System are shown in Table 10, in which the identification score is 94.3 (% ID). The identity of this isolate is confirmed to be *Lactobacillus acidophilus*;
(iii) The isolate X21B7 of the present invention is identified to be *Lactobacillus acidophilus* by the Micro-IS System, in which the obtained results are shown in Table 7, and the identification score is 0.682 (ID score);
(iv) The 16S rDNA sequence analysis result of the isolate X21B7 of the present invention is shown in FIG. 8. After a comparison with DNA databases (MICROSEQ Reference Manual, 1999, PE CO., USA), it was found that the 16S rDNA sequence (SEQ ID NO:4) of the isolate X21B7 of the present invention is most homologous to the 16S rDNA sequence of *Lactobacillus gasseri* ($B_1$ group in *Lactobacillus acidophilus*); and
(v) According to the above-mentioned identification results, the isolate X21B7 of the present invention is most probably *Lactobacillus gasseri*, subgroup $B_1$ of *Lactobacillus acidophilus*.

TABLE 10

```
Reference: X21B7
GOOD IDENTIFICATION
```

```
Strip: API 50 CHL
Profile: ---------- ++?------- --++-++++- -+-------+ ----------
  0    - GLY  - ERY  - DARA - LARL - RIB - DXYL - LXYL - ADO - MDX  - GAL  +
 GLU   + FRU  ? MNE  - SBE  - RHA - DUL  - INO  - MAN - SOR - MDM  - MDG  -
 NAG   + AMY  + ARB  - ESC  + SAL + CEL  + MAL  + LAC - MEL - SAC  + TRE  -
 INU   - MLZ  - RAE  - AMD  - GLYG- XLT  - GEN  + TUR - LYX - TAG  - DEUC -
 LFUC  - DARL - LARL - GNT  - 2KG - 5KG  -
```

| Significant taxa | | % Id. | T | Tests against |
|---|---|---|---|---|
| Lacto. Acidophilus | 1 | 94.3 | 0.65 | 2 |
| Next choice | | | | |
| Pedio. Damnosus | 2 | 2.0 | 0.43 | 3 |
| Lacto. acidophilus | | 1:2 test(s) against | | |
| D-MANNOSE | (MNE) | 96% TREHALOSE | (TRE) | 77% |

5. Isolate B38T38 of the Present Invention
(i) According to the preliminary identification results, the isolate B38T38 is gram-positive, catalase negative and non-mobile, and it grows under both aerobic and anaerobic conditions;
(ii) The test results using API 50 CHL identification kit of the API System are shown in Table 11, in which the identification score is 90.8 (% ID). The identity of this isolate is confirmed to be *Lactobacillus acidophilus*;
(iii) The isolate B38T38 of the present invention is identified to be *Lactobacillus acidophilus* by the Micro-IS System, in which the obtained results are shown in Table 12, and the identification score is 0.646 (ID score);
(iv) The 16S rDNA sequence analysis result of the isolate B38T38 of the present invention is shown in FIG. 9. After a comparison with DNA databases (MICROSEQ Reference Manual, 1999, PE CO., USA), it was found that the 16S rDNA sequence (SEQ ID NO:5) of the isolate B38T38 of the present invention is most homologous to the 16S rDNA sequence of *Lactobacillus gasseri* ($B_1$ group in *Lactobacillus acidophilus*); and (v) According to the above-mentioned identification results, the isolate B38T38 of the present invention is most probably *Lactobacillus gasseri*, subgroup $B_1$ of *Lactobacillus acidophilus*.

TABLE 11

```
Reference: B38T38
GOOD IDENTIFICATION
```

```
Strip: API 50 CHL
Profile: ---------- ++++------ --+-+++++- -++------+ ----------
   0  - GLY - ERY  - DARA - LARL - RIB - DXYL - LXYL - ADO - MDX -  GAL +
  GLU + FRU + MNE  + SBE  - RHA  - DUL - INC  - MAN  - SOR - MDM -  MDG -
  NAG + AMY - ARB  + ESC  + SAL  + CEL + MAL  + LAO  - MEL - SAC +  TRE +
  INU - MLZ - RAE  - AMD  - GLYG - XLT - GEN  + TUR  - LYX - TAG -  DFUC -
 LFUC - DARL - LARL - GNT  - 2KG  - 5KG -
```

| Significant taxa | | % Id. | T | Tests against |
|---|---|---|---|---|
| Lacto. acidophilus | 1 | 90.8 | 0.93 | 0 |
| Next choice | | | | |
| Lacto. delb.lactis | 2 | 6.2 | 0.74 | 2 |
| Lacto. acidophilus | | 1:0 test(s) against | | |

TABLE 12

Micro-IS System
Strain name: B38T38

| | | | | |
|---|---|---|---|---|
| − | 013001 MOTILITY | − | 006001 | ENDOSPORES |
| − | 017013 GROWTH 15° C. | + | 017017 | GROWTH 45° C. |
| + | 016059 AEROBIC GROWTH | − | 024045 | GLUCOSE TO $CO_2$ |
| − | 028528 GLUCONATE, GAS | + | 025203 | AMYGDALIN, ACID |
| − | 025181 L-ARABINOSE, ACID | + | 025211 | CELLOBIOSE, ACID |
| + | 025193 D-FRUCTOSE, ACID | + | 025194 | D-GALACTOSE, ACID |
| + | 025195 D-GLUCOSE, ACID | + | 025212 | LACTOSE, ACID |
| + | 025213 MALTOSE, ACID | − | 026371 | D-MANNITOL, ACID |
| + | 025196 D-MANNOSE, ACID | + | 025217 | MELEZITOSE, ACID |
| + | 025214 MELIBIOSE, ACID | + | 025218 | RAFFINOSE, ACID |
| − | 025191 L-RHAMNOSE, ACID | − | 025184 | D-RIBOSE, ACID |
| + | 025210 SALICIN, ACID | − | 026374 | D-SORBITOL, ACID |
| + | 025215 SUCROSE, ACID | + | 025216 | TREHALOSE, ACID |
| − | 025186 D-XYLOSE, ACID | − | 028060 | L-MALATE UTIL |

| *DIAGNOSIS* | **ID SCORE | **LIKELIHOOD | **BESTLIKEL. |
|---|---|---|---|
| 1 *L. delbrueckll* ssp lactis | 0.64607 | 0.145038024 | 0.4351140 |
| 2 *L. acidophilus* | 0.35240 | 0.079110108 | 0.0791101 |

| SUGGESTED TE | VALUE IN SETVALUE ALONE |
|---|---|
| 1 024029 (L+) LACTATE PROD | 2 |
| 2 029268 L-ARGININE DEAM | 2 |

6. Isolate B6T7 of the Present Invention (i) According to the preliminary identification results, the isolate B6T7 is gram-positive, catalase negative and non-mobile, and it grows under both aerobic and anaerobic conditions;

(ii) The test results using API 50 CHL identification kit of the API System are shown in Table 13, in which the identification score is 92.4 (% ID). The identity of this isolate is confirmed to be *Lactobacillus plantarum*;

(iii) The isolate B6T7 of the present invention is identified to be *Lactobacillus acidophilus* by the Micro-IS System, in which the obtained results are shown in Table 7, and the identification score is 0.682 (ID score);

(iv) The 16S rDNA sequence analysis result of the isolate B6T7 of the present invention is shown in FIG. 10. Since the identification results obtained with the API 50 CHL identification kit and those obtained with the Micro-IS System identification system classify the isolate B6T7 of the present invention to be *Lactobacillus plantarum* and *Lactobacillus acidophilus* of *Lactobacillus*, respectively, the 16S rDNA sequence (SEQ ID NO: 6) of the isolate B6T7 of the present invention was compared with the 16S rDNA sequence of *Lactobacillus acidophilus* (SEQ ID NO:7) and that of *Lactobacillus plantarum* (SEQ ID NO:8). It was found that the 16S rDNA sequence of the isolate B6T7 (SEQ ID NO:6) of the present invention is most homologous to the 16S rDNA sequence of *Lactobacillus acidophilus*, and differs greatly from the 16S rDNA sequence of *Lactobacillus plantarum*; and (v) According to the above identification results, the isolate B6T7 of the present invention is most probably *Lactobacillus acidophilus*.

TABLE 13

```
Reference: B6T7
DOUBTFUL PROFILE

Strip: API 50 CHL
Profile: ----++---- ++++-+--+- --+++-++++ +++--+---+ ----------
   0   - GLY - ERY - DARA - LARL + RIB + DXYL - LXYL - ADO - MDX -  GAL +
 GLU + FRU + MNE + SBE  - RHA  + DUL - INO  - MAN  + SOR - MDM -  MDG -
 NAG + AMY + ARB + ESC  - SAL  + GEL + MAL  + LAC  + MEL + SAC +  TRE +
 INU - MLZ - RAF + AMD  - GLYG - XLT - GEN  + TUR  - LYX - TAG -  DFUC -
 LFUC - DARL - LARL - GNT - 2KG - 5KG -
```

| Significant taxa | | % Id. | T | Tests against |
|---|---|---|---|---|
| Lacto. plantarum | 1 | 92.4 | 0.59 | 3 |
| Next choice | | | | |
| Lacto. salivarius | | 3.4 | 0.45 | 4 |
| Lacto. plantarum | | 1:3 test(s) against | | |
| D-SORBITOL | (SPR) | 75% | ESCULINE (ESC) | 99% |
| MELEZITOSE | (MLE) | 92% | | |

Summarizing the identification results, all of the six isolates screened in accordance with the present invention belong to *Lactobacillus* strains, in which B6T7 is *Lactobacillus acidophilus*, and B21T1, B21T6, C21T1, X21B7 and B38T38 are *Lactobacillus gasseri*, subgroup $B_1$ of *Lactobacillus acidophilus*.

Referring to Table 14, as compared with *Lactobacillus* strains disclosed in prior patents and literatures, the six *Lactobacillus* isolates obtained in accordance with the present invention not only can grow in an environment containing 0.3% bile salts, but also have higher survival rates and a good cholesterol-lowering ability after being cultured in an acidic environment of pH 2 for 2 hours. In addition, the six *Lactobacillus* isolates of the present invention have the ability to co-precipitate with cholesterol and assimilate cholesterol. It is apparent that the isolates of the present invention and their sub-cultured offsprings are excellent probiotic bacteria, and can be used in the manufacture of food products, such as beverages, cakes, infant foods, fermented milk, dietary supplements, and animal feed. Also, they can be used in the manufacture of pharmaceutical compositions for the treatment and prevention of gastrointestinal diseases and lowering serum cholesterol.

For examples, *Lactobacillus* isolates obtained in accordance with the present invention can be used in the manufacture of lactic acid beverages and yogurt drinks with reference to Referential Example 1 and Referential Example 2 disclosed in U.S. Pat. No. 5,516,684.

TABLE 14

Comparison of the isolates of the present invention with known strains disclosed in prior patents and literatures

| Strains | Sources of isolation | Characteristics | patent/literature |
|---|---|---|---|
| L. acidophilus GG (ATCC 53103) | Human | 1. Bile salt tolerance<br>It can grow in an environment containing 0.15% bile acids.<br>2. Acid tolerance<br>It can grow up to $10^9$ CFU in an pH 5 environment.<br>It can grow up to $10^7$ CFU in an pH 3 environment.<br>Population decreased within 2 log values after being grown in pH 2.5 gastric juice for 30 minutes.<br>Survived cells after treatment at pH 1–2 for 2 hrs were measured to be $10^3$ CFU.<br>3. Lowering of cholesterol<br>It lowered the excretion amount of cholesterol in human feces. | US 4839281<br>US 5032399 |
| L. acidophilus LA16 | Male pig | 1. Lowering of cholesterol<br>A decrease of serum cholesterol by 60% (in a system containing 0.4% oxgall and 10 mg cholesterol).<br>Animal tests revealed that after a feeding time of 56 days, serum cholesterol was decreased by 10.5% and LDL-cholesterol content was decreased by 9%.<br>(Note: LA16 is a L. acidophilus strain isolated from the feces of pigs which had been fed with yogurt containing L. acidophilus DDS-1(human source) and having the ability of lowering cholesterol.) | Danielson et al., 1989 |

TABLE 14-continued

Comparison of the isolates of the present invention with known strains disclosed in prior patents and literatures

| Strains | Sources of isolation | Characteristics | patent/literature |
|---|---|---|---|
| *L. acidophilus* ATCC 43121 ATCC 4356 | Pig<br>Human | 1. Bile salt tolerance<br>The $OD_{620\ nm}$ values of the two strains were increased by 0.3 units after being cultured in an environment containing 0.3% oxgall for 2.93 and 7.4 hours, respectively.<br>2. Lowering of cholesterol<br>A decrease of serum cholesterol by 55.4% and 12.9%, respectively, after being cultured in a system containing 0.3% oxgall and 0.1% PPLO for 14 hrs. | Gilliland and Walker, 1990 |
| *L. gasseri* SBT 0274 SBT 0270 | Human | 1. Bile salt tolerances<br>The two strains can grow in an environment containing 0.3% oxgall.<br>2. Acid tolerance<br>Population decreased 2 log values after being grown at pH 2.5, 37° C. for 3 hrs.<br>Population decreased 4~5 log values after being grown at pH 1.5, 37° C. for 2 hrs<br>3. Lowering of cholesterol<br>A decrease of cholesterol content by 47% and 36%, respectively, after being cultured in a system containing 0.3% oxgall and 100 μg cholesterol micelle/ml for 20 hrs. | Usman and Hosono, 1999 |
| *L. gasseri* B21T1 B21T6 C21T1 X21B7 B38T38 *L. acidophilus* B6T7 | Healthy infants | 1. Bile salt tolerance<br>80% survived, i.e. population decreased 0.5–2 log values after being grown in an environment containing 0.3% oxgall for 24 hrs.<br>2. Acid tolerance<br>Population decreased 3~4 log values after being treated at pH 2, 37° C. for 2 hrs (0.85% NaCl/0.01 N HCl system)<br>3. Lowering of cholesterol<br>A decrease of cholesterol content by 93% or higher after anaerobic culture in MRS broth containing 0.3% oxgall and 12% horse serum for 24 hrs.<br>A decrease of cholesterol content by 25~45% after anaerobic culture in MRS broth containing 0.3% oxgall and 12% cholesterol micelles for 24 hrs.<br>A cholesterol assimilation rate reached 12~40%. | The invention strains |

Note:
ATCC 43121 = CCRC 17064
ATCC 4356 = CCRC 10695
PPLO (BACT PPLO SERUM FRACTION) was produced by DIFCO LABORARORIES, but this product has not been produced presently.

All patents and references cited herein are hereby incorporated by reference in their entirety. In case of conflict, the present description, including definitions, will prevail.

While the present invention has been described with reference to the above specific embodiments, it is apparent that numerous modifications and variations can be made without departing from the scope and spirit of this invention. It is therefore intended that this invention be limited only as indicated by the appended claims.

We claim:

1. An isolated *Lactobacillus* strain being : (I) a deposited strain selected from:
   a) *Lactobacillus gasseri* B21T1 deposited with the American Type Culture Collection under an accession number ATCC PTA-4483;
   b) *Lactobacillus gasseri* B21T6 deposited with the American Type Culture Collection under an accession number ATCC PTA-4484;
   c) *Lactobacillus gasseri* C21T1 deposited with the American Type Culture Collection under an accession number ATCC PTA-4479;
   d) *Lactobacillus gasseri* X21 B7 deposited with the American Type Culture Collection under an accession number ATCC PTA-4480;
   e) *Lactobacillus gasseri* B38T38 deposited with the American Type Culture Collection under an accession number ATCC PTA-4481; or
   f) *Lactobacillus acidophilus* B6T7 deposited with the American Type Culture Collection under an accession number ATCC PTA-4482.

2. A food product comprising an edible material and an isolated *Lactobacillus* strain according to claim 1.

3. The food product of claim 2, wherein the edible material is selected from the group consisting of fluid milk products, fermented milk, milk powder, ice cream, cream cheese, dry cheese, bean milk and fermented bean milk, fruit-vegetable juices, fruit juices, sports drinks, dessert, candy, infant formulas, health food products, animal feed, and dietary supplements.

4. The food product of claim 2, which is manufactured in the form of an instant food.

5. An oral dosage form of a pharmaceutical composition comprising the isolated *Lactobacillus* strain according to claim 1, wherein the oral dosage form is a solution, emulsion, powder, tablet, or capsule.

6. The food product of claim 2, further comprising at least a probiotic microorganism selected from the group consisting of *Lactobacillus* sp., *Streptococcus* sp., yeasts, and a combination thereof.

7. The food product of claim 6, wherein the *Lactobacillus* sp. is any one of *Lactobacillus acidophilus*, *Lactobacillus lactis*, *Lactobacillus brevis*, *Lactobacillus casei*, *Lactobacillus plantarum*, *Lactobacillus salivarius*, *Lactobacillus bifidus*, *Lactobacillus bulgaricus*, *Lactobacillus causasicus* and *Lactobacillus rhamnosus*.

8. The food product of claim 6, wherein the *Streptococcus* sp. is *Streptococcus thermophilus* or *Streptococcus lactis*.

9. The food product of claim 6, wherein the yeast is *Candida kefyr* or *Saccharomyces florentinus*.

* * * * *

SEQUENCE LISTING

<160> NUMBER OF SEQ ID NOS: 8

<210> SEQ ID NO 1
<211> LENGTH: 500
<212> TYPE: DNA
<213> ORGANISM: Lactobacillus gasseri B21T1

<400> SEQUENCE: 1

```
caggacgaac gctggcggcg tgcctaatac atgcaagtcg agcgagcttg cctagatgaa      60
tttggtgctt gcaccaaatg aaactagata caagcgagcg gcggacgggt gagtaacacg     120
tgggtaacct gcccaagaga ctgggataac acctggaaac agatgctaat accggataac     180
aacactagac gcatgtctag agtttaaaag atggttctgc tatcactctt ggatggacct     240
gcggtgcatt agctagttgg taaggtaacg gcttaccaag gcaatgatgc atagccgagt     300
tgagagactg atcggccaca ttgggactga gacacggccc aaactcctac gggaggcagc     360
agtagggaat cttccacaat ggacgcaagt ctgatggagc aacgccgcgt gagtgaagaa     420
gggtttcggc tcgtaaagct ctgttggtag tgaagaaaga tagaggtagt aactggcctt     480
tatttgacgg taattactta                                                500
```

<210> SEQ ID NO 2
<211> LENGTH: 500
<212> TYPE: DNA
<213> ORGANISM: Lactobacillus gasseri B21T6

<400> SEQUENCE: 2

```
caggacgaac gctggcggcg tgcctaatac atgcaagtcg agcgagcttg cctagatgaa      60
tttggtgctt gcaccaaatg aaactagata caagcgagcg gcggacgggt gagtaacacg     120
tgggtaacct gcccaagaga ctgggataac acctggaaac agatgctaat accggataac     180
aacactagac gcatgtctag agtttaaaag atggttctgc tatcactctt ggatggacct     240
gcggtgcatt agctagttgg taaggtaacg gcttaccaag gcaatgatgc atagccgagt     300
tgagagactg atcggccaca ttgggactga gacacggccc aaactcctac gggaggcagc     360
agtagggaat cttccacaat ggacgcaagt ctgatggagc aacgccgcgt gagtgaagaa     420
gggtttcggc tcgtaaagct ctgttggtag tgaagaaaga tagaggtagt aactggcctt     480
tatttgacgg taattactta                                                500
```

<210> SEQ ID NO 3
<211> LENGTH: 500
<212> TYPE: DNA
<213> ORGANISM: Lactobacillus gasseri C21T1

<400> SEQUENCE: 3

```
caggacgaac gctggcggcg tgcctaatac atgcaagtcg agcgagcttg cctagatgaa      60
tttggtgctt gcaccaaatg aaactagata caagcgagcg gcggacgggt gagtaacacg     120
tgggtaacct gcccaagaga ctgggataac acctggaaac agatgctaat accggataac     180
aacactagac gcatgtctag agtttaaaag atggttctgc tatcactctt ggatggacct     240
gcggtgcatt agctagttgg taaggtaacg gcttaccaag gcaatgatgc atagccgagt     300
tgagagactg atcggccaca ttgggactga gacacggccc aaactcctac gggaggcagc     360
agtagggaat cttccacaat ggacgcaagt ctgatggagc aacgccgcgt gagtgaagaa     420
gggtttcggc tcgtaaagct ctgttggtag tgaagaaaga tagaggtagt aactggcctt     480
tatttgacgg taattactta                                                500
```

<210> SEQ ID NO 4
<211> LENGTH: 500
<212> TYPE: DNA
<213> ORGANISM: Lactobacillus gasseri X21B7

<400> SEQUENCE: 4

```
caggacgaac gctggcggcg tgcctaatac atgcaagtcg agcgagcttg cctagatgat      60
tttggtgctt gcactaaatg aaactagata caagcgagcg gcggacgggt gagtaacacg     120
tgggtaacct gcccaagaga ctgggataac acctggaaac agatgctaat accggataac     180
aacactagac gcatgtctag agtttgaaag atggttctgc tatcactctt ggatggacct     240
gcggtgcatt agctagttgg taaggtaacg gcttaccaag gcaatgatgc atagccgagt     300
tgagagactg atcggccaca ttgggactga gacacggccc aaactcctac gggaggcagc     360
agtagggaat cttccacaat ggacgaaagt ctgatgagc aacgccgcgt gagtgaagaa      420
gggtttcggc tcgtaaagct ctgttggtag tgaagaaaga tagaggtagt aactggcctt     480
tatttgacgg taattactta                                                  500

<210> SEQ ID NO 5
<211> LENGTH: 500
<212> TYPE: DNA
<213> ORGANISM: Lactobacillus gasseri B38T38

<400> SEQUENCE: 5
caggacgaac gctggcggcg tgcctaatac atgcaagtcg agcgagcttg cctagatgaa      60
tttggtgctt gcaccaaatg aaactagata caagcgagcg gcggacgggt gagtaacacg     120
tgggtaacct gcccaagaga ctgggataac acctggaaac agatgctaat accggataac     180
aacactagac gcatgtctag agtttaaaag atggttctgc tatcactctt ggatggacct     240
gcggtgcatt agctagttgg taaggtaacg gcttaccaag gcaatgatgc atagccgagt     300
tgagagactg atcggccaca ttgggactga gacacggccc aaactcctac gggaggcagc     360
agtagggaat cttccacaat ggacgcaagt ctgatgagc aacgccgcgt gagtgaagaa      420
gggtttcggc tcgtaaagct ctgttggtag tgaagaaaga tagaggtagt aactggcctt     480
tatttgacgg taattactta                                                  500

<210> SEQ ID NO 6
<211> LENGTH: 480
<212> TYPE: DNA
<213> ORGANISM: Lactobacillus acidophilus B6T7

<400> SEQUENCE: 6
cagacgaacg ctggcggcgt gcctaataca tgcaagtcga gcgacctgaa ccaacagatt      60
cacttcggtg atgacgttgg gaacgcgagc ggcggatggg tgagtaacac gtggggaccc     120
tgccccatag tctgggatac cacttggaaa caggtgcaat accggataag aaagcagatg     180
ccatgatcag cttataaaag gcggcgtaag ctgtcgctat gggatggccc cgcggtgcat     240
tagctagttg gtagggtaac ggcctaccaa ggcaatgatg catagccgag tttgagagac     300
tgatccggcc acattgggac tgagacacg cccaaactcc tacgggaggg caagcagtag     360
ggaatcctcc acaatggacc aaagtcctga tggagcaacg ccccgtgagt tgaagaagtt     420
ttcggatcgt aaagccctgt tgttggtgaa gaaggataga ggtaagaact ggcctttatt     480

<210> SEQ ID NO 7
<211> LENGTH: 480
<212> TYPE: DNA
<213> ORGANISM: Lactobacillus acidophilus

<400> SEQUENCE: 7
caggacgaac gctggcggcg tgcctaatac atgcaagtcg agcgagctga accaacagat      60
```

```
tcacttcggt gatgcagttg ggaacgcgag cggcggatgg gtgagtaaca cgtggggaac    120
ctgccccata gtctgggata ccacttggaa acaggtgcaa taccggataa gaaagcagat    180
gccatgatca gcttataaaa ggcggcgtaa gctgtcgcta tgggatggcc ccgcggtgca    240
ttagctagtt ggtagggtaa cggcctacca aggcaatgat gcatagccga gttgagagac    300
tgatcggcca cattgggact gagacacggc ccaaactcct acgggaggca gcagtaggga    360
atcttccaca atgacgaaa gtctgatgga gcaacgccgc gtgagtgaag aaggttttcg    420
gatcgtaaag ctctgttgtt ggtgaagaag gatagaggta gtaactggcc tttatttgac    480

<210> SEQ ID NO 8
<211> LENGTH: 480
<212> TYPE: DNA
<213> ORGANISM: Lactobacillus plantarum

<400> SEQUENCE: 8
caggacgaac gctggcggcg tgcctaatac atgcaagtcg aacgaactct ggtattgatt     60
ggtgcttgca tcatgattta catttgagtg agtggcgaaa tggtgagtaa cavgtgggaa    120
acctgcccag aagcgggga taacacctgg aaacagatgc taataccgca taacaacttg    180
gaccgcatgg tccgagttga aagatggctt cggctatcac ttttggatgg tcccgcggcg    240
tattagctag atgctggggt aacggctcac catggcaatg atacgtagcc gacctgagag    300
ggtaatcggc cacattggga ctgagacacg gcccaaactc ctacgggagg cagcagtagg    360
gaatcttcca caatggacga aagtctgatg gagcaacgcc gcgtgagtga agaagggttt    420
cggctcgtaa aactctgttg ttaaagaaga acatatctga gagtaactgt tcaggtattg    480
```